(12) United States Patent
Brasier et al.

(10) Patent No.: US 12,092,640 B2
(45) Date of Patent: Sep. 17, 2024

(54) METHODS AND COMPOSITIONS FOR DIAGNOSIS OF RICKETTSIA INFECTION

(71) Applicant: THE BOARD OF REGENTS OF THE UNIVERSITY OF TEXAS SYSTEM, Austin, TX (US)

(72) Inventors: Allan R. Brasier, Galveston, TX (US); Yingxin Zhao, Galveston, TX (US); David H. Walker, Galveston, TX (US); Rong Fang, Galveston, TX (US)

(*) Notice: Subject to any disclaimer, the term of this patent is extended or adjusted under 35 U.S.C. 154(b) by 402 days.

(21) Appl. No.: 17/004,309

(22) Filed: Aug. 27, 2020

(65) Prior Publication Data

US 2021/0063394 A1 Mar. 4, 2021

Related U.S. Application Data

(60) Provisional application No. 62/892,048, filed on Aug. 27, 2019.

(51) Int. Cl.
*G01N 33/53* (2006.01)
*G01N 33/563* (2006.01)
*G01N 33/569* (2006.01)

(52) U.S. Cl.
CPC ..... *G01N 33/56911* (2013.01); *G01N 33/563* (2013.01)

(58) Field of Classification Search
CPC ................................................. G01N 33/56911
See application file for complete search history.

(56) References Cited

U.S. PATENT DOCUMENTS

2003/0003508 A1* 1/2003 Raoult ............. G01N 33/56911
435/7.1

OTHER PUBLICATIONS

Patel et al (Bio. Chem. Vol. 401 (2), pp. 249-262) (Year: 2020).*
Anderson et al., "The Human Plasma Proteome" *Molecular & Cellular Proteomics* 2002, 1.11, 845-867.
Baixauli et al., "Exosomes and autophagy: coordinated mechanisms for the maintenance of cellular fitness" *Frontiers in Immunology* 2014, 5(403), 1-6.
Bechah et al., "Rickettsia prowazekii infection of endothelial cells increases leukocyte adhesion through $X_v\beta_3$ integrin engagement" *Clinical Microbiology and Infection* 2009, 15, 249-250.
Bechelli et al., "Atg5 Supports Rickettsia australis Infection in Macrophages In Vitro and In Vivo" *Infection and Immunity* 2019, 87(1), 1-19.
Bechelli et al., "MyD88 Mediates Instructive Signaling in Dendritic Cells and Protective Inflammatory Response during Rickettsial Infection" *Infection and Immunity* 2016, 84(4), 883-893.
Broadhurst et al., "Laboratory Evaluation of a Dot-Blot Enzyme Immunoassay for Serologic Confirmation of Illness Due to Rickettsia Conorii" *Am. J. Trop. Med. Hyg.* 1998, 58(6), 786-789.

Chan et al., "Rickettsial outer-membrane protein B (rOmpB) mediates bacterial invasion through Ku70 in an actin, c-Cbl, clathrin and caveolin 2-dependent manner" *Cellular Microbiology* 2009, 11(4), 629-644.
Chapman, Alice S., *Diagnosis and Management of Tickborne Rickettsia/Diseases: Rocky Mountain Spotted Fever, Ehrlichioses, and Anaplasmosis—United States*. MMWR CDC, 2006.
Clifton et al., "Expression and secretion of chemotactic cytokines IL-8 and MCP-1 by human endothelial cells after Rickettsia rickettsii infection: Regulation by nuclear transcription factor NF-κB" *International Journal of Medical Microbiology* 2005, 295, 267-278.
Cox et al. "Accurate Proteome-wide Label-free Quantification by Delayed Normalization and Maximal Peptide Ratio Extraction, Termed MaxLFQ" *Molecular & Cellular Proteomics* 2014, 13.9, 2513-2526.
Cox et al., "Andromeda: A Peptide Search Engine Integrated into the MaxQuant Environment" *Journal of Proteome Research* 2011, 10, 1794-1805.
Cox et al., "MaxQuant enables high peptide identification rates, individualized p.p.b.-range mass accuracies and proteome-wide protein quantification" *Nature Biotechnology* 2008, 26(12), 1367-1372.
Damas et al., "Relative chemokine and adhesion molecule expression in Mediterranean spotted fever and African tick bite fever" *Journal of Infection* 2009, 58, 68-75.
Demory-Beckler et al., "Proteomic analysis of exosomes from mutant KRAS colon cancer cells identifies intercellular transfer of mutant KRAS" *Molecular & Cellular Proteomics* 2013, 49 pages.
Dignat-George et al., "Rickettsia conorii Infection Enhances Vascular Cell Adhesion Molecule-1- and Intercellular Adhesion Molecule-1-Dependent Mononuclear Cell Adherence to Endothelial Cells" *The Journal of Infectious Diseases* 1997, 175, 1142-52.
Egertson et al., "Multiplexed peptide analysis using data-independent acquisition and Skyline" *Nature Protocols* 2015, 10(6), 887-903.
Elomaa et al., "Structure of the Human Macrophage MARCO Receptor and Characterization of Its Bacteria-binding Region" *The Journal of Biological Chemistry* 1998, 273(8), 4530-4538.
Gabay et al., "Acute-Phase Proteins and Other Systemic Responses to Inflammation" *The New England Journal of Medicine* 1999, 448-456.
Gaudet et al., "Phylogenetic-based propagation of functional annotations within the Gene Ontology consortium" *Briefings in Bioinformatics* 2011, 12(5), 449-62.
Heinzen et al., "Directional Actin Polymerization Associated with Spotted Fever Group Rickettsia Infection of Vero Cells" *Infection and Immunity* 1993, 61(5), 1926-1935.
Jeng et al., "A Rickettsia WASP-like protein activates the Arp2/3 complex and mediates actin-based motility" *Cellular Microbiology* 2004, 6(8), 761-769.

(Continued)

*Primary Examiner* — Albert M Navarro

(57) ABSTRACT

Certain embodiments are directed to detection methods and methods of identifying detection targets for sensitive and specific laboratory tests to diagnose and monitor rickettsial infections during the earliest stages of the disease and to assess the degree of illness.

6 Claims, 17 Drawing Sheets

Specification includes a Sequence Listing.

(56) References Cited

OTHER PUBLICATIONS

Kaplanski et al., "IL-6 and IL-8 Production from Cultured Human Endothelial Cells Stimulated by Infection with Rickettsia conorii via a Cell-associated IL-1α-dependent Pathway" *J. Clin. Invest.* 1995, 96, 2839-2844.
Keerthikumar et al., "ExoCarta: A web-based compendium of exosomal cargo" *Journal of Molecular Biology* 2015, 17 pages.
Lange et al., "Selected reaction monitoring for quantitative proteomics: a tutorial" *Molecular Systems Biology* 2008, 4(222), 1-14.
MacLean et al., "Skyline: an open source document editor for creating and analyzing targeted proteomics experiments" *Bioinformatics* 2010, 26(7), 966-968.
Makridakis et al., "Secretome proteomics for discovery of cancer biomarkers" *Journal of Proteomics* 2010, 73, 2291-2305.
Mansueto et al., "New Insight into Immunity and Immunopathology of Rickettsial Diseases" *Clinical and Developmental Immunology* 2012, 26 pages.
Maroto et al., "Effects of storage temperature on airway exosome integrity for diagnostic and functional analyses" *Journal of Extracellular Vesicles* 2017, 6, 19 pages.
Martinez et al., "Early signaling events involved in the entry of Rickettsia conorii into mammalian cells" *Journal of Cell Science* 2004, 117, 5097-5106.
Martinez et al., "Ku70, a Component of DNA-Dependent Protein Kinase, Is a Mammalian Receptor for Rickettsia conorii" *Cell* 2005, 123, 1013-1023.
Osterloh, Anke. "Immune response against rickettsiae: lessons from murine infection models" *Med Microbiol Immunol* 2017, 206, 403-417.
Otterdal et al., "Rickettsia conorii is a potent complement activator in vivo and combined inhibition of complement and CD14 is required for attenuation of the cytokine response ex vivo" *Clinical Microbiology and Infection* 2016, 22, 734.e1-734.e6.
Paddock et al., "Hidden Mortality Attributable to Rocky Mountain Spotted Fever: Immunohistochemical Detection of Fatal, Serologically Unconfirmed Disease" *The Journal of Infectious Diseases* 1999, 179, 1469-76.
Perez-Riverol et al., "The PRIDE database and related tools and resources in 2019: improving support for quantification data" *Nucleic Acids Research* 2019, 47, D442-D450.
Prunotto et al., "Proteomic analysis of podocyte exosome-enriched fraction from normal human urine" *Journal of Proteomics* 2013, 82, 193-229.
Renesto et al., "Identification and Characterization of a Phospholipase D-Superfamily Gene in Rickettsiae" *The Journal of Infectious Diseases* 2003, 188, 1276-83.
Rovery et al., "Questions on Mediterranean Spotted Fever a Century after Its Discovery" *Emerging Infectious Diseases* 2008, 14(9), 1360-1367.
Schaechter et al., "Study on the Growth of Rickettsiae II. Morphologic Observations of Living Rickettsiae in Tissue Culture Cells" *Virology* 1957, 3, 160-172.
Schilling et al., "Multiplexed, Scheduled, High-Resolution Parallel Reaction Monitoring on a Full Scan QqTOF Instrument with Integrated Data-Dependent and Targeted Mass Spectrometric Workflows" *Analytical Chemistry* 2015, 87, 10222-10229.
Silverman et al., "Potential for Free Radical-Induced Lipid Peroxidation as a Cause of Endothelial Cell Injury in Rocky Mountain Spotted Fever" *Infection and Immunity* 1988, 56(12), 3110-3115.
Sporn et al., "E-Selection-Dependent Neutrophil Adhesion to Rickettsia rickettsia-Infected Endothelial Cells" *Blood* 1993, 81(9), 2406-2412.
Sporn et al., "Interleukin-1α Production during Rickettsia rickettsii Infection of Cultured Endothelial Cells: Potential Role in Autocrine Cell Stimulation" *Infection and Immunity* 1996, 64(5), 1609-1613.
Sporn et al., "Rickettsia rickettsia Infection of Cultured Human Endothelial Cells Induces NF-κB Activation" *Infection and Immunity* 1997, 65(7), 2786-2791.
Teysseire et al., "Intracellular movements of Rickettsia conorii and R. typhi based on actin polymerization" *Res. Microbiol.* 1992, 143, 821-829.
Toprak et al., "Conserved Peptide Fragmentation as a Benchmarking Tool for Mass Spectrometers and a Discriminating Feature for Targeted Proteomics" *Molecular & Cellular Proteomics* 2014, 13.8, 2056-2071.
Tyanova et al., "The Perseus computational platform for comprehensive analysis of (prote)omics data" *Nature Methods* 2016, 13(9), 731-740.
Uchiyama et al., "Restriction of the growth of a nonpathogenic spotted fever group rickettsia" *FEMS Immunol Med Microbiol* 2012, 64, 42-47.
Valbuena et al., "Effect of Blocking the CXCL9/10-CXCR3 Chemokine System in the Outcome of Endothelial-Target Rickettsial Infections" *Am. J. Trop. Med. Hyg.* 2004, 71(4), 393-399.
Valbuena et al., "Expression Analysis of the T-Cell-Targeting Chemokines CXCL9 and CXCL10 in Mice and Humans with Endothelial Infections Caused by Rickettsiae of the Spotted Fever Group" *American Journal of Pathology* 2003, 163(4), 1357-1369.
Valbuena et al., "Infection of the endothelium by members of the order Rickettsiales" *Thromb Haemost.* 2009, 102(6), 1071-1079.
Videm et al., "Soluble ICAM-1 and VCAM-1 as Markers of Endothelial Activation" *Scandinavian Journal of Immunology* 2008, 67, 523-531.
Walker et al., "Establishment of a Novel Endothelial Target Mouse Model of a Typhus Group Rickettsiosis: Evidence for Critical Roles for Gamma Interferon and CD8 T Lymphocytes" *Laboratory Investigation* 2000, 80(9), 1361-1372.
Walker et al., "Human Endothelial Cell Culture Plaques Induced by Rickettsia rickettsia" *Infection and Immunity* 1982, 37(1), 301-306.
Walker et al., "Pathogenic Mechanisms of Diseases Caused by Rickettsia" *Ann. N.Y. Acad. Sci.* 2003, 990, 1-11.
Walker et al., "Penetration of Cultured Mouse Fibroblasts (L Cells) by Rickettsia prowazeki" *Infection and Immunity* 1978, 22(1), 200-208.
Walker et al., "Rickettsia Conorii Infection of C3H/HeN Mice A Model of Endothelial-Target Rickettsiosis" *Laboratory Investigation* 1994, 70(3), 358-368.
Whitworth et al., "Expression of the Rickettsia prowazekii pld or tlyC Gene in *Salmonella enterica* Serovar Typhimurium Mediates Phagosomal Escape" *Infection and Immunity* 2005, 73(10), 6668-6673.
Zhang et al., "Quantitative Assessment of the Effects of Trypsin Digestion Methods on Affinity Purification—Mass Spectrometry-based Protein-Protein Interaction Analysis" *J. Proteome Res.* 2017, 16, 3068-3082.
Zhao et al., "Applications of Selected Reaction Monitoring (SRM)-Mass Spectrometry (MS) for Quantitative Measurement of Signaling Pathways" *Methods* 2013, 61(3), 313-322.
Zhao et al., "Endothelial Cell Proteomic Response to Rickettsia conorii Infection Reveals Activation of the Janus Kinase (JAK)-Signal Transducer and Activator of Transcription (STAT)-Inferferon Stimulated Gene (ISG) 15 Pathway and Reprogramming Plasma Membrane Integrin/Cadherin Signaling" *Molecular & Cellular Proteomics* 2015, 15.1, 289-304.
Zhao et al., "Quantification of Activated NF-B/RelA Complexes Using ssDNA Aptamer Affinity-Stable Isotope Dilution—Selected Reaction Monitoring—Mass Spectrometry" *Molecular & Cellular Proteomics* 2011, 10.6, 17 pages.
Zhao et al., "Systematic Analysis of Cell-Type Differences in the Epithelial Secretome Reveals Insights into the Pathogenesis of Respiratory Syncytial Virus-Induced Lower Respiratory Tract Infections" *J Immunol.* 2017, 198, 3345-3364.

* cited by examiner

FIG. 19

METHODS AND COMPOSITIONS FOR DIAGNOSIS OF RICKETTSIA INFECTION

PRIORITY CLAIM

The present application claims priority to U.S. Provisional Application No. 62/892,048 filed Aug. 27, 2019 which is incorporated herein by reference.

STATEMENT REGARDING FEDERALLY FUNDED RESEARCH

This invention was made with government support under TR001439 awarded by the National Institutes of Health (NIH). The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

*Rickettsia* spp., gram-negative obligatly intracellular alphaproteobacteria, are of global medical and veterinary health importance due to their endemicity and re-emergence. From the clinical and antigenic perspective, rickettsial diseases are classified in two groups, spotted fever and typhus. The spotted fever group rickettsiae are transmitted by ticks and include a number of species. The most virulent are *R. rickettsii*, the agent of Rocky Mountain spotted fever, and *R. conorii*, the agent of Mediterranean spotted fever (boutonneuse fever), a disease prevalent throughout the Mediterranean, Africa, the Middle East, and India. In humans, the spotted fevers present as acute fever, headache, maculopapular rash, and vascular leakage that can lead to significant morbidity and mortality due to pulmonary and cerebral edema, particularly if there are delays in diagnosis or treatment. There is a need for early diagnosis and administration of treatments as soon as possible.

Infections caused by spotted fever rickettsiae can result in hospitalization, development of complications, and, not infrequently, death in previously healthy individuals of any age. Unfortunately, correct diagnosis still depends on clinical suspicion and a rapid response to empirical treatment with doxycycline. In addition, in tropical areas, there is a long list of febrile syndromes with similar initial clinical presentation. Most of these diseases are of viral etiology (e.g., dengue); thus, the subjects presenting with febrile symptoms are not administered antibiotic treatment.

There remains a need for additional methods and compositions for diagnosing early (differentiating from similar presenting viral infections) and initiating treatment for *Rickettsia* infections as soon as possible.

SUMMARY

One of the major problems with effectively controlling spotted fever rickettsioses is the lack of a specific diagnostic assay to detect the acute stage of infections. The clinical diagnosis of a rickettsial infection relies on the patient's symptoms, history of possible exposure to infected arthropods or travel to an endemic area, and supporting data from laboratory diagnostic assays. However, the current laboratory diagnostic assays for spotted fever rickettsioses are problematic because they are: (1) Too late for physicians to make a specific and prompt treatment plan. At present, serology is the gold standard for diagnosis of spotted fever rickettsioses. However, antibody response often occurs after a time at which treatment is effective; detection of an antibody response is too late. (2) Diagnostics are not reliable. While molecular detection of bacterial DNA and immunohistochemical analysis of rickettsial antigen in the skin biopsy specimens could yield a diagnosis during the acute stage of rickettsial infection, only 40-50% of the patients present with rash or eschar. (3) Diagnostics are not sufficiently sensitive. Because of the endothelial tropism of rickettsiae, molecular genetic approaches often have poor sensitivity in blood samples, except in the late phase of fatal cases. (4) Diagnostics may not be applicable. Laboratory isolation and culture of rickettsiae from clinical samples for diagnosis require technical expertise and specialized facilities, a biosafety level-3 laboratory. Such facilities may not be readily accessible. Thus, early diagnostic assays for spotted fever rickettsioses are urgently needed.

One solution to the above described problems is the development of detection methods and identification of detection targets for sensitive and specific laboratory tests to diagnose and monitor rickettsial infections during the earliest stages of the disease and to assess the degree of illness (host response).

In certain aspects, Rickettsial protein RC0497 (SEQ ID NO:1) can be measured in a sample, e.g., body fluids (plasma, serum, urine), to diagnose rickettsial infection. In specific aspects, tryptic peptides of RC0497 can be detected. The peptides include peptides having, consisting essentially of, or consisting of the amino acid sequence HDLVGLGEVTVNR (SEQ ID NO:2), LLLSLDSTGEK (SEQ ID NO:3), ELAEAGFGR (SEQ ID NO:4), SDFPAEQIGK, (SEQ ID NO:5), EYHNDLTDQAFYAGK (SEQ ID NO:6), EYGYGVESTSTFDQFTQQAVR (SEQ ID NO:7), and/or GASVHYIIDK (SEQ ID NO:8). RC0497 protein or peptide fragments thereof can be measured in body fluids (plasma, serum, urine) alone or in combination for diagnosing rickettsial infection. In certain embodiments the protein and the peptide fragments can be derived from SEQ ID NO:9, SEQ ID NO:10, or a peptide of FIG. 19.

In certain aspects, circulating RC0497 or its tryptic peptides can be detected to diagnose *R conorii* (Mediterranean spotted fever) or *R rickettsii* (Rocky Mountain spotted fever) infections. In certain aspects the sample is affinity enriched for one or more peptides. Certain embodiments include affinity enrichment-mass spectrometry method (IP-SRM or IP-PRM) for detection of circulating RC0497 or its tryptic peptides in a sample of a subject. In certain aspects, the subject has a rickettsial infection or is suspected of being exposed to *rickettsia*, or is or has been present in a geographic region where rickettsial infections are prevalent. Rickettsial strains to be detected can include *R. conorii, R. rickettsii, R. monacensis, R. amblyommates, R. parkeri, R. sibirica, R. africae, R. phihpii, R. japonica* and others (see Table 1).

In certain embodiments a group of host response proteins can be evaluated. The levels of host response proteins can be indicative or used in combination with the rickettsial peptides described herein to determine mild versus severe rickettsial infections (i.e., used as an indicator of prognosis). In certain aspects, a panel of RC0497 and/or fragments thereof and a panel of host response proteins can be used to indicate or assess treatment options and/or treatment response. One embodiment includes a clinical test to diagnose rickettsial infection. One embodiment includes a number of clinical tests over time to monitor the results of treating a rickettsial infection. A panel of rickettsial and host response proteins can be used as an indicator of the response to therapy and to monitor therapeutic efficacy of a treatment.

A "sample" or "biological sample" in terms of the invention means a sample of biological tissue or fluid. Examples of biological samples are sections of tissues, blood, blood fractions, plasma, serum, urine or samples from other peripheral sources. A biological sample may be provided by removing a sample of cells from a subject, but can also be provided by using a previously isolated sample. For example, a tissue sample can be removed from a subject suspected of having a disease by conventional biopsy techniques. In a preferred embodiment, a blood sample is taken from the subject. According to the invention, the biological sample preferably is a blood or a serum sample.

"Polypeptide" refers to any peptide or protein comprising amino acids joined by peptide bonds or modified peptide bonds. "Polypeptide" refers to short chains, including peptides, oligopeptides or oligomers, and to longer chains, including proteins.

"Substantially similar" with respect to amino acid sequences, means at least about 65% identity between two or more sequences. Preferably, the term refers to at least about 70% identity between two or more sequences, more preferably at least about 75% identity, more preferably at least about 80% identity, more preferably at least about 85% identity, more preferably at least about 90% identity, more preferably at least about 91% identity, more preferably at least about 92% identity, more preferably at least about 93% identity, more preferably at least about 94% identity, more preferably at least about 95% identity, more preferably at least about 96% identity, more preferably at least about 97% identity, more preferably at least about 98% identity, and more preferably at least about 99% or greater identity. Such identity can be determined using algorithms known in the art, such as the mBLAST algorithm.

"Antibody" refers to all isotypes of immunoglobulins (IgG, IgA, IgE, IgM, IgD, and IgY) including various monomeric and polymeric forms of each isotype, unless otherwise specified.

"Functional fragments" of such antibodies comprise portions of intact antibodies that retain antigen-binding specificity of the parent antibody molecule. For example, functional fragments can comprise at least the CDRs of either the heavy chain or light chain variable region. Functional fragments can also comprise the heavy chain or light chain variable region, or sequences that are substantially similar to the heavy or light chain variable region. Further suitable functional fragments include, without limitation, antibodies with multiple epitope specificity, bispecific antibodies, diabodies, and single-chain molecules, as well as Fab, F(ab')2, Fd, Fabc, and Fv molecules, single chain (Sc) antibodies (also called ScFv), individual antibody light chains, individual antibody heavy chains, chimeric fusions between antibody chains and other molecules, heavy chain monomers or dimers, light chain monomers or dimers, dimers consisting of one heavy and one light chain, and the like. All antibody isotypes can be used to produce functional fragments of the antibodies herein. Functional fragments can be recombinantly or synthetically produced, with natural or unnatural nucleic acid or amino acid molecules.

The antibodies or functional fragments thereof of the disclosed subject matter can be generated from any species. The antibodies or functional fragments thereof described herein can be labeled or otherwise conjugated to various chemical or biomolecule moieties, for example, for therapeutic or diagnostic or detection or treatment applications. The moieties can be cytotoxic, for example, bacterial toxins, viral toxins, radioisotopes, and the like. The moieties can be detectable labels, for example, fluorescent labels, radiolabels, biotin, and the like, which are known in the art.

Antibodies of the present invention can be used to detect the various proteins and peptide described, the antibodies can be labeled with a detectable moiety, such as enzymes or fluorophores. There are a wide variety of fluorophore labels that can usefully be attached to the antibodies of the present invention. Common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCPCy5.5, PE-Cy5, PE-Cy5.5, PE-Cy7, PE-Texas Red, and APC-Cy7. Other fluorophores include, inter alia, Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, OR, USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, OR, USA), and Cy2, Cy3, Cy3.5, Cy5, Cy5.5, Cy7, all of which are also useful for fluorescently labeling the antibodies of the present invention. For secondary detection using labeled avidin, streptavidin, captavidin or neutravidin, the antibodies of the present invention can usefully be labeled with biotin. When the antibodies of the present invention are used, e.g., for western blotting applications, they can usefully be labeled with radioisotopes, such as $^{33}$P, $^{32}$P, $^{35}$S, $^{3}$H, and $^{125}$I.

An "anti-RC0497 antibody" described herein detects or binds an epitope of RC0497 protein. An anti-RC0497 antibody can comprise a light chain variable region and a heavy chain variable region.

The antibodies or functional fragments thereof described herein have binding affinities (in M) for RC0497 or peptides thereof that include a dissociation constant (KD) of less than $1 \times 10^{-2}$. In some embodiments, the KD is less than $1 \times 10^{-3}$. In other embodiments, the KD is less than $1 \times 10^{-4}$. In some embodiments, the KD is less than $1 \times 10^{-5}$. In still other embodiments, the KD is less than $1 \times 10^{-6}$. In other embodiments, the KD is less than $1 \times 10^{-7}$. In other embodiments, the KD is less than $1 \times 10^{-8}$.

The terms "treating" or "treatment" refer to any success or indicia of success in the attenuation or amelioration of a rickettsial infection, including any objective or subjective parameter such as abatement, diminishing of symptoms such as fever, pulmonary or cerebral edema. The treatment or amelioration of symptoms can be based on objective or subjective parameters; including the results of a physical examination, neurological examination, and/or psychiatric evaluations.

As used herein, the term "subject" refers to any mammal, including both human and other mammals. Preferably, the methods of the present invention are applied to human subjects.

As used herein, the term "antigen" is a molecule capable of being bound by an antibody. The structural aspect of an antigen, e.g., three-dimensional conformation or modification, is referred to herein as an "antigenic determinant" or "epitope." Thus, antigenic determinants or epitopes are those parts of an antigen that are recognized by antibodies. An antigenic determinant need not be a contiguous sequence or segment of protein and may include various sequences that are not immediately adjacent to one another, i.e., a conformational epitope.

The term "antibody" or "immunoglobulin" is used to include intact antibodies and binding fragments/segments thereof. Typically, fragments compete with the intact antibody from which they were derived for specific binding to an antigen. Fragments include separate heavy chains, light chains, Fab, Fab' F(ab')2, Fabc, and Fv. Fragments/segments can be produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibodies. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, Clin Exp Immunol 79:315-21, 1990; Kostelny et al., J. Immunol. 148:1547-53, 1992.

The term "isolated" can refer to a polypeptide that is substantially free of cellular material, bacterial material, viral material, or culture medium (when produced by recombinant DNA techniques) of their source of origin, or chemical precursors or other chemicals (when chemically synthesized).

Moieties of the invention, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation."

"Prognosis" refers to a prediction of how a patient will progress, and whether there is a chance of recovery. "Rickettsiosis prognosis" generally refers to a forecast or prediction of the probable course or outcome of a rickettsial infection. As used herein, prognosis includes the forecast or prediction of any one or more of the following: duration of survival of a patient—and/or response rate in a group of patients susceptible to or diagnosed with a rickettsiosis. Prognosis also includes prediction of favorable responses to treatments, such as a conventional antibiotic therapy.

In one embodiment, the marker level is compared to a reference level representing the same marker. A reference level may be a reference level of from a different subject or group of subjects know to have or not having rickettsial infection. The reference level may be a single value or may be a range of values. The reference level can be determined using any method known to those of ordinary skill in the art. In some embodiments, the reference level is an average level of expression determined from a cohort of subjects serving as negative or positive controls/reference. The reference level may comprise data obtained at the same time (e.g., in the same hybridization experiment) as the patient's individual data, or may be a stored value or set of values, e.g., stored on a computer, or on computer-readable media. If the latter is used, new patient data for the selected marker(s), obtained from initial or follow-up samples, can be compared to the stored data for the same marker(s) without the need for additional control experiments.

The phrase "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein/peptide. For example, solid-phase ELISA immunoassays are routinely used to select monoclonal antibodies specifically immunoreactive with a protein. See, e.g., Harlow and Lane, Antibodies: A Laboratory Manual, Cold Spring Harbor Press, 1988, for a description of immunoassay formats and conditions that can be used to determine specific immunoreactivity.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 19. Protein multiple sequence alignment of N-acetyl-muramoyl-L-alanine amidase from different rickettsia strains. The peptides that were identified by MS were highlighted in red, green, and blue.

DESCRIPTION

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be an example of that embodiment, and not intended to intimate that the scope of the disclosure, including the claims, is limited to that embodiment.

The clinical manifestations of acute MSF are a consequence of the tropism of rickettsiae for endothelial cells. Rickettsial organisms bind Ku70 on cholesterol-rich microdomains and enter endothelial cells through a calcium-dependent zipper-like entry mechanism. Viable organisms subsequently lyse intracellular phagosomes via phospholipase D and hemolysin activities, and replicate in the cytoplasm. A characteristic of the spotted fever group is that *R. conorii* organisms spread intercellularly as a consequence of directional actin polymerization without producing early cellular injury. Oxidative stress produced by replication of *R. conorii* results in peroxidation of endothelial membranes and disruption of the endothelial barrier function producing vascular leakage.

The pulmonary and cerebral edema in patients infected with rickettsiae can lead to significant morbidity and mortality if there are delays in diagnosis and treatment. The reference standard for diagnosis of rickettsial diseases is a fourfold rise in antibody titer by the indirect immunofluorescence assay (IFA) assay using paired serum samples obtained soon after illness and 2-4 weeks later. Patients usually do not have diagnostic serum antibody titers during the first week of illness, and a negative result by IFA does not exclude the diagnosis. Therefore, many cases are initially misdiagnosed accounting for adverse outcomes, and consequently, the epidemiology of the disease is under-reported. A highly specific and sensitive biomarker for early diagnosis of rickettsial infection is greatly needed.

The RC0479 protein has been found in both in vitro cell culture and in vivo animal models of spotted fever rickettsial infections by using an affinity enrichment-mass spectrometry method (IP-SRM or IP-PRM). RC0497 is a diagnostic biomarker for spotted fever rickettsioses. Embodiments are directed to diagnostic assays developed by detecting this biomarker. These assays are expected to provide specific diagnostic information at the early stage of spotted fever rickettsioses when treatment can make a difference in patient management.

Figure 1:
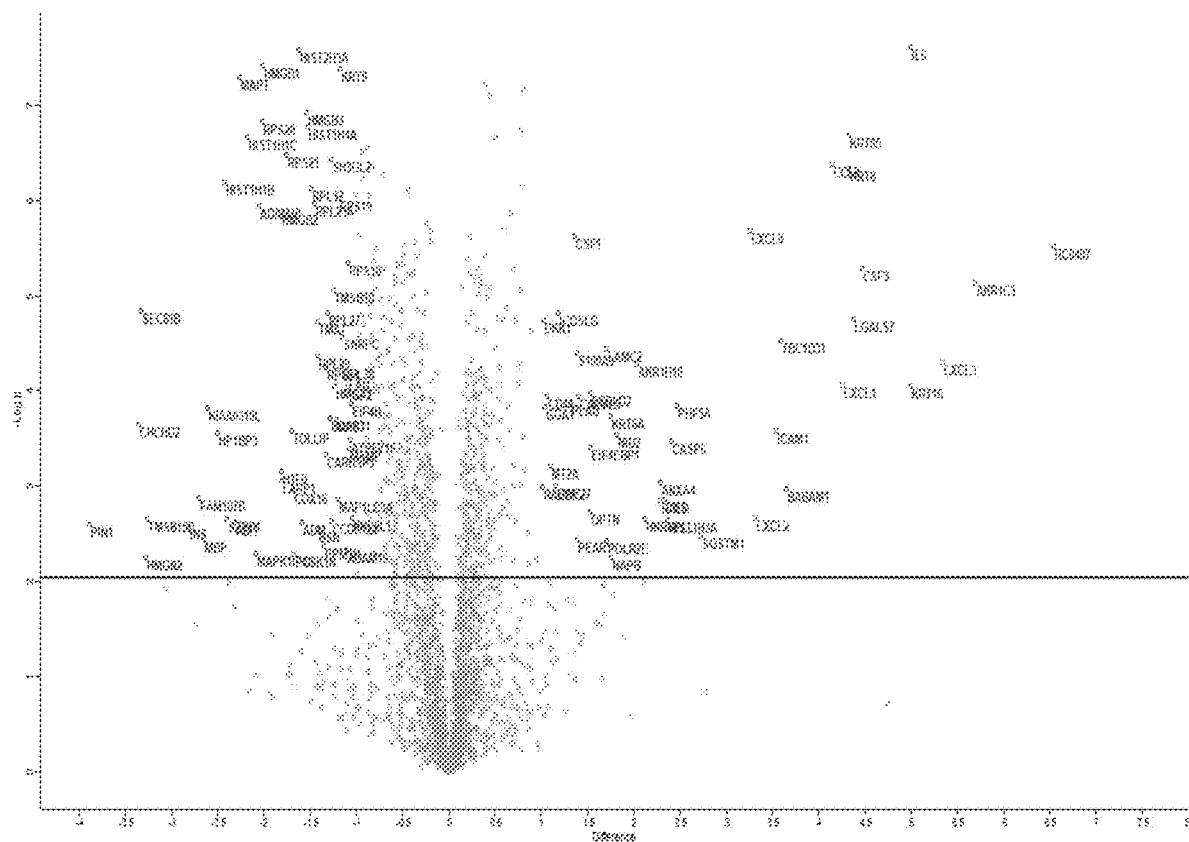
FIG. 1. Differential expression of proteins. Shown are the difference (X axis) and the statistical confidence (Y axis) for proteins identified in R conorii-infected endothelial cells. Note RC0497 labeled in the top right quadrant of the graph.

The protein RC0497 (SEQ ID NO:1) was detected in high concentrations in cell culture supernatant and with high confidence (FIG. 1). Over 11 peptides of the same protein were identified. Among the identified peptides are four proteotyptic peptides (a peptide unique for the target protein). These peptides are HDLVGLGEVTVNR (SEQ ID NO:2), LLLSLDSTGEK (SEQ ID NO:3), ELAEAGFGR (SEQ ID NO:4), and SDFPAEQIGK (SEQ ID NO:5). Interestingly, these peptides correspond to a subdomain of RC0497. SRM and PRM assays were developed using these proteotypic peptides for quantifying RC0497. The RC0497 protein was detectable in C57BL/6 mice infected with sublethal or lethal inoculations of R conorii. Plasma obtained from these mice was analyzed for changes in protein/peptide levels.

Rickettsial proteins were identified as diagnostic in vivo. Plasma samples from four animal groups (17 samples in total) Group 1: uninfected (n=5 mice); Group 2: sub-lethal dose (n=6 mice); Group 3: lethal dose (n=3 mice); and Group 4 dead (n=3 mice). The plasma samples were subjected to four analyses: (1) Global protein profiling without prefraction of plasma proteins or peptides; (2) Targeted profiling for rickettsia protein RC0497 using selected reaction monitoring (SRM); (3) targeted profiling for RC0497 using parallel reaction monitoring (PRM); and (4) strong cation exchange (SCX) chromatography-LC-MS/MS analysis.

Figures 2, 3:
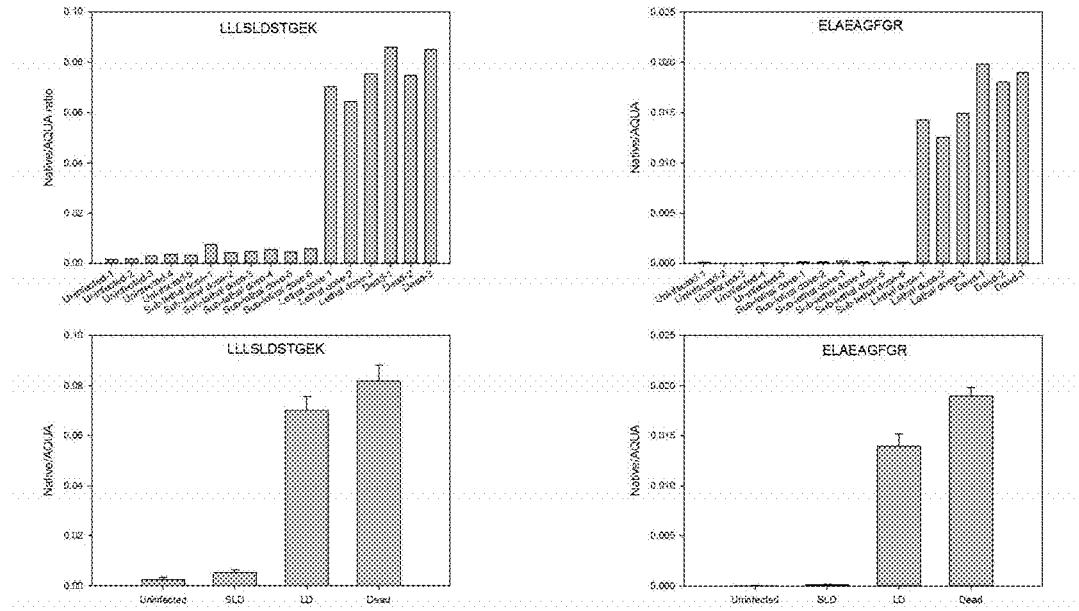
FIG. 2. Detection of RC0497 in mouse plasma from R conorii infection in vivo. Shown is the measurement of two R conorii peptides, LLLSLDSTGEK (SEQ ID NO:3), and ELAEAGFGR (SEQ ID NO:4), respectively. Top panel is measurement for each individual mouse in the experiment. Bottom is collated results.
FIG. 3. Peptide alignment of RC407 peptides with R conorii (Q92IC3, SEQ ID NO:9) and R rickettsii (strain Iowa)(BOBX83, SEQ ID NO:10).

The first attempt of global protein profiling without using any forms of prefraction technology primarily identified a panel of host response proteins that associate with disease severity. RC0497 was not identified in this experiment primarily due to the interference from high-abundance host proteins in mass spectrometry analysis. Two proteotypic peptides of RC0497, LLLSLDSTGEK (SEQ ID NO:3) and ELAEAGFGR (SEQ ID NO:4), were identified in sublethally and lethally infected mice by PRM. Shown in FIG. 2 are the results for LLLSLDSTGEK (SEQ ID NO:3), ELAEAGFGR (SEQ ID NO:4). The results are similar, with the peptide abundance statistically higher with the sublethal (SL) infection than that seen in control mice, and a dramatic increase in the mice with lethal infection (FIG. 2). In addition to the two RC0497 peptides identified by PRM, four additional peptides were identified by strong cation exchange chromatography (SCX) approach. These peptides are GASVHYIIDK (SEQ ID NO:8), EYHNDLTDQAFYAGK (SEQ ID NO:6), HDLVGLGEVTVNR (SEQ ID NO:2), and EYGYGVESTSTFDQFTQQAVR (SEQ ID NO:7).

RC0497 is conserved in spotted fever strains. Analysis indicates that RC0497 and the diagnostic tryptic peptides are highly conserved across rickettsial strains (FIG. 3, Table 1). FIG. 3 shows the alignment of Q92IC3 from R. conorii with the same protein in Rickettsia rickettsii. R. rickettsii is the causative agent of the Rocky Mountain spotted fever (RMSF) and is the prototype bacterium in the spotted fever group of rickettsiae. These data indicate that the diagnostic approach will be useful in the detection of both Mediterranean spotted fever and Rocky Mountain spotted fever infections.

Proteotypic peptides are conserved in the Rickettsia genus. Conservation of the proteotypic peptides for RC0497 were analyzed in regard to other known Rickettsia species. In addition to R. conorii, and R. rickettsii, the diagnostic peptides are found in R. conorii, R. rickettsii, R. monacensis, R. amblyommates, R. parkeri, R. sibirica, R. africae, R. phihpii, R. japonica and others These data indicate that the IP-SRM and IP-PRM assays will be diagnostic for a wide variety of rickettsial infections.

Host response proteins. The understanding of the host response to rickettsial infection has been advanced by the development of a standardized model of endothelial cell infection using primary human umbilical vein cells (HUVECs). Proteomics were applied for measurement and identification of rickettsial proteins in the golgi, plasma membrane, or secreted proteins. The proteins selected are based on the identification of specific protein fragments in infected human endothelial cells, which could not be predicted based on available genomic sequence. Similarly, the host response proteins are combinations of proteins that represent the endothelial response to infection.

Figure 4:
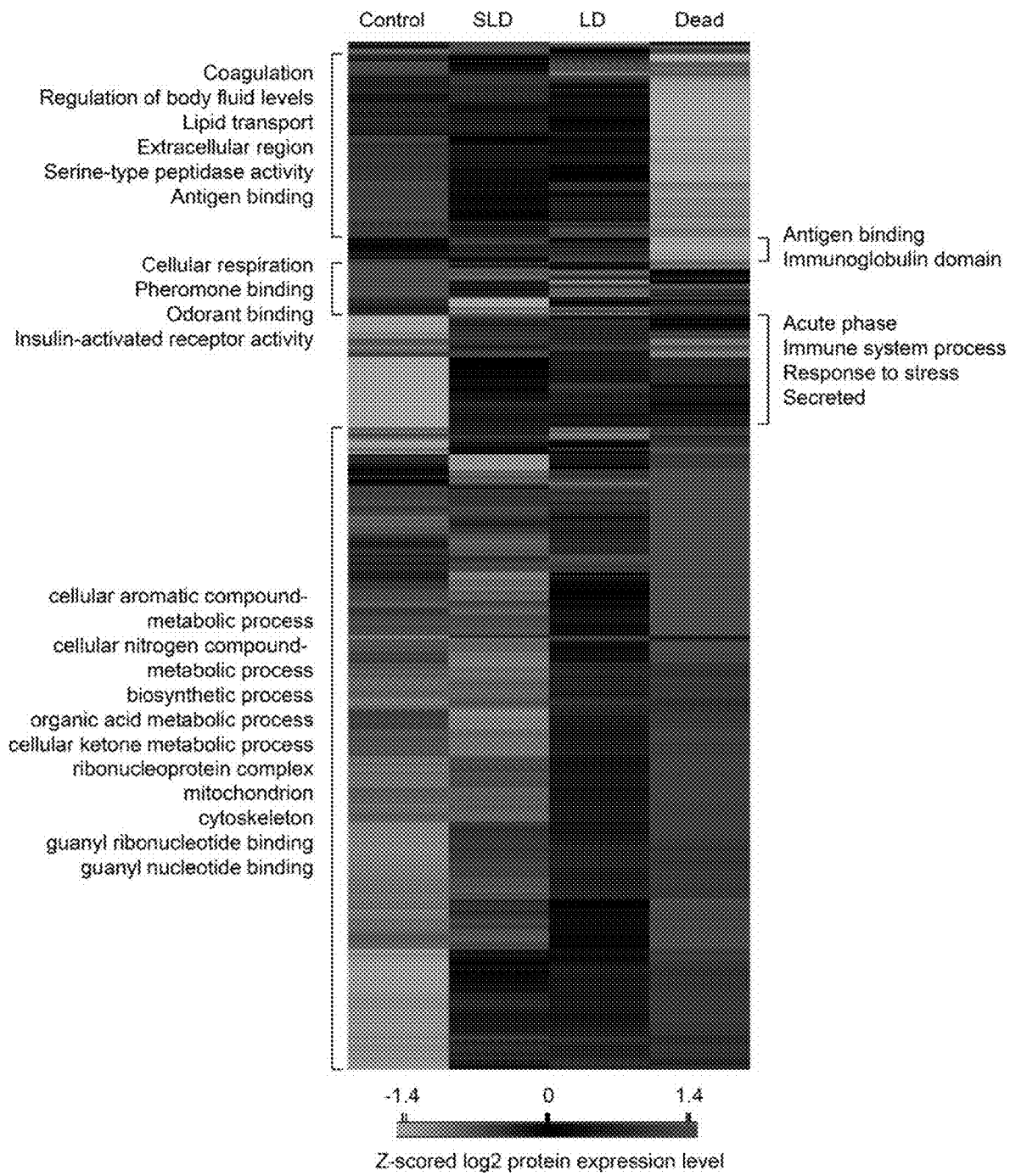
FIG. 4. Protein expression and protein GO function annotation analysis. Shown is the statistically changed proteins grouped by expression for the control, sublethal and lethal infections. For each cluster, the proteins are grouped by biological process.

Identification of host response proteins were extended to those associated with sublethal vs lethal infections. Distinct protein profiles were obtained for each disease type as shown in the heat map in FIG. 4. In FIG. 4, sublethal infections are characterized by a group of proteins associated with the acute phase response and immune system processes. By contrast, the lethally infected protein patterns are associated with intracellular proteins. The measurement of acute phase response proteins and intracellular proteins are indicative of the host response and the severity of infection.

Figure 5:
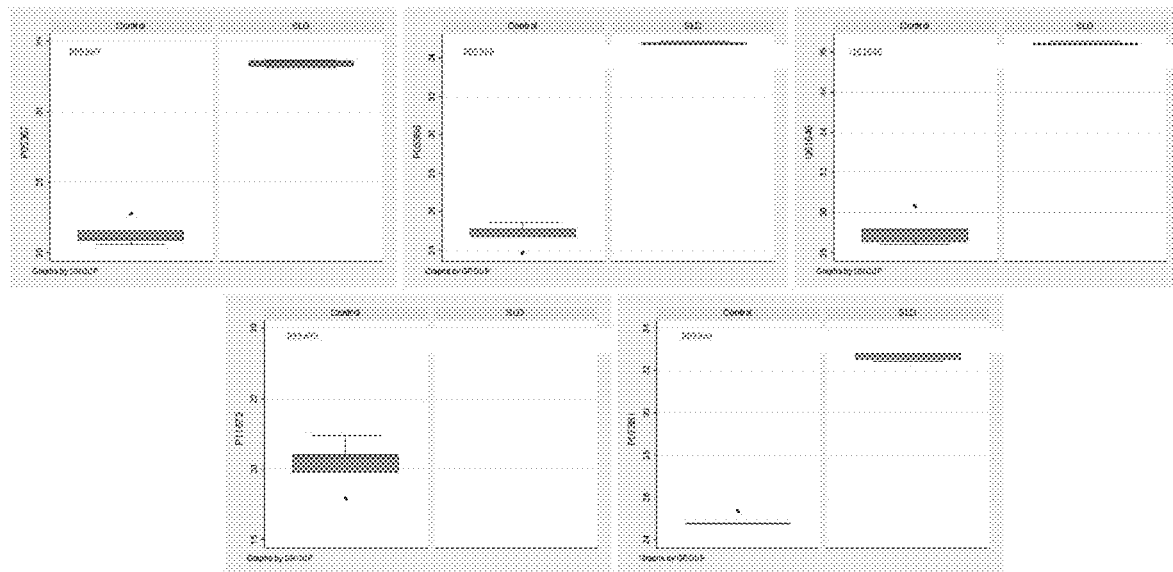
FIG. 5. Expression of top 5 proteins separating sublethal disease (SLD) vs control infections. For each protein in Table 2, the abundance of the protein measured in plasma is plotted. For each box plot, shown is the 25-75% interquartile range with the mean (horizontal line). Outliers are indicated by *.

Identification of protein panel that differentiates sublethal disease (SLD) from control. The differentially expressed proteins were subjected to statistical analysis for microarray (SAM) to identify those proteins that were significantly different by outcome. Over 140 proteins were significant; of these the top 5 informative markers are shown in Table 2 below. The protein distribution is shown in FIG. 5. As shown in FIG. 4, these proteins are enriched in acute phase reactants.

TABLE 1

| Entry | Protein names | Gene names | Organism | SEQ ID NO: 2 | SEQ ID NO: 7 | SEQ ID NO: 6 | SEQ ID NO: 8 | SEQ ID NO: 4 | SEQ ID NO: 3 | SEQ ID NO: 5 |
|---|---|---|---|---|---|---|---|---|---|---|
| A0A067AM61 | N-acetyl-anhydromuranmyl-L-alanine amidase | REISMN_00610 | *R. buchneri* | + | + | + | + | + | | |
| A0A0B7J056 | N-acetyl-anhydromuranmyl-L-alanine amidase | RMONA_05350 | *R. monacensis* | + | + | + | + | + | | |
| A0A0F3N2F2 | N-acetylmuramoyl-L-alanine amidase family protein | APHACPA_0989 | *Candidatus Rickettsia amblyommii* str. Ac/Pa | | + | + | | + | + | |
| A0A0F3PEE8 | N-acetylmuramoyl-L-alanine amidase family protein | RMAECT_1144 | *R. rhipicephali* str. Ect | + | + | + | + | + | + | |
| A0A0F3QSA8 | N-acetylmuramoyl-L-alanine amidase family protein | RAMDARK_0700 | *Candidatus Rickettsia amblyommii* str. Darkwater | | + | + | | + | + | |
| A0A0F3RBQ6 | N-acetylmuramoyl-L-alanine amidase family protein | REIP_0615 | *Rickettsia endosymbiont of Ixodes pacificus* | + | + | + | + | + | | |
| A0A0F3RHM9 | N-acetylmuramoyl-L-alanine amidase family protein | RAT170B_0454 | *Rickettsia argasii* T170-B | + | + | + | + | + | + | |
| A0A0H3AUD9 | Uncharacterized protein | A1G_02815 | *Rickettsia rickettsii* (strain Sheila Smith) | + | + | + | + | + | + | |
| A8EZ72 | Uncharacterized protein | A1E_03620 | *Rickettsia canadensis* (strain McKiel) | + | | | | | | |
| A8F1D6 | Negative regulator of beta-lactamase expression | ampD1 RMA_0515 | *Rickettsia massiliae* (strain Mtu5) | + | + | + | + | | + | |
| B0BX83 | Anhydro-N-acetylmuramyl-tripeptide amidase (EC 3.5.1.28) | RrIowa_0591 | *Rickettsia rickettsii* (strain Iowa) | + | + | + | + | + | + | |
| C3PN80 | Negative regulator of beta-lactamase expression | ampD1 RAF_ORF0464 | *Rickettsia africae* (strain ESF-5) | + | + | + | + | | + | + |
| C4YU55 | Anhydro-N-acetylmuramyl-tripeptide amidase | REIS_0949 | *Rickettsia endosymbiont of Ixodes scapularis* | + | + | + | + | + | | |
| G0GXT0 | Negative regulator of beta-lactamase expression | Rh054_02850 | *Rickettsia heilongjiangensis* (strain ATCC VR-1524/054) | + | + | + | + | + | + | |
| G4KMU9 | AmpD protein homolog | ampD1 RJP_0391 | *Rickettsia japonica* (strain ATCC VR-1363/YH) | + | + | + | + | + | + | |
| H6PTD5 | Negative regulator of beta-lactamase expression | RSA_02760 | *Rickettsia philipii* (strain 364D) | + | + | + | + | + | + | |
| H6QJL2 | Negative regulator of beta-lactamase expression | RMB_05550 | *Rickettsia massiliae* str. AZT80 | + | + | + | + | + | + | |
| H8K515 | Negative regulator of beta-lactamase expression | MCE_03350 | *Rickettsia amblyommii* (strain GAT-30V) | | + | + | + | + | + | |

TABLE 1-continued

| Entry | Protein names | Gene names | Organism | SEQ ID NO: 2 | SEQ ID NO: 7 | SEQ ID NO: 6 | SEQ ID NO: 8 | SEQ ID NO: 4 | SEQ ID NO: 3 | SEQ ID NO: 5 |
|---|---|---|---|---|---|---|---|---|---|---|
| H8KDD6 | Negative regulator of beta-lactamase expression | MCI_06710 | Rickettsia montanensis (strain OSU 85-930) | + | + | + | + | + | + | |
| H8KHL4 | Negative regulator of beta-lactamase expression | MCC_03370 | Rickettsia rhipicephali (strain 3-7-female6-CWPP) | + | | + | + | + | | |

TABLE 2

| Sublethal vs control Protein ID | Common Name | Lethal vs sublethal Protein ID | Common Name |
|---|---|---|---|
| P05367 | Serum amyloid A-2 protein | P07743 | BPI fold-containing family A member 2 |
| P05366 | Serum amyloid A-1 protein | P84244 | Histone H3.3 |
| Q61646 | Haptoglobin | P09528 | Ferritin heavy chain |
| P11672 | Neutrophil gelatinase-associated lipocalin | P49429 | 4-hydroxy-phenylpyruvate dioxygenase |
| Q9JM99-4 | Proteoglycan 4 | P40124 | Adenylyl cyclase-associated protein 1 |

Figure 6:
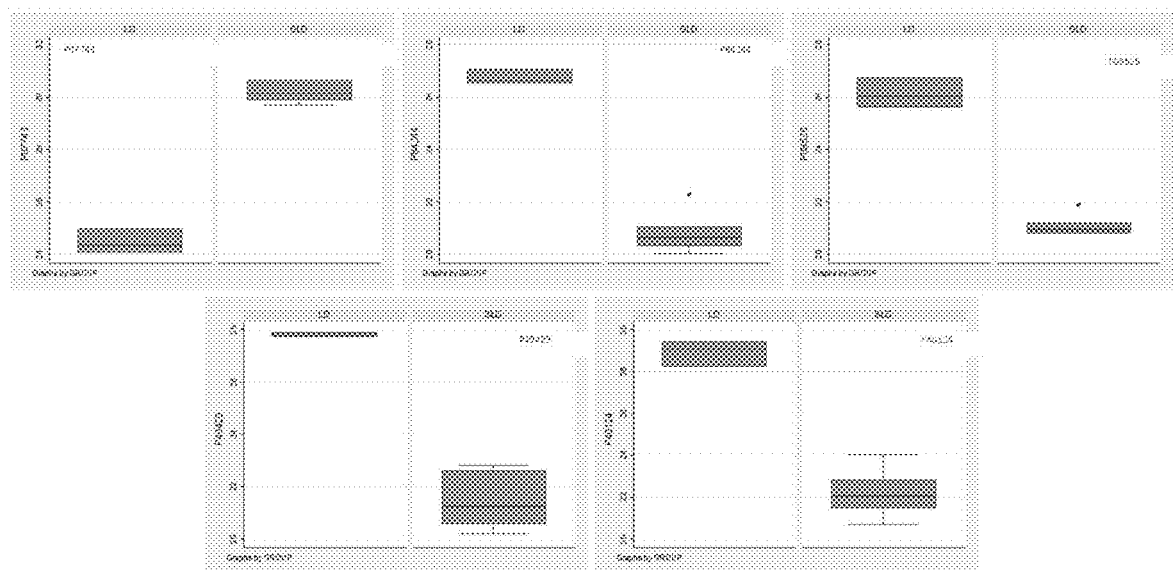
FIG. 6. Expression of top 5 proteins separating lethal disease (LD) vs sublethal disease (SLD). For each protein in Table 2, the abundance of the protein measured in plasma is plotted. For each box plot, shown is the 25-75% interquartile range with the mean (horizontal line). Outliers are indicated by *.
Figure 7:
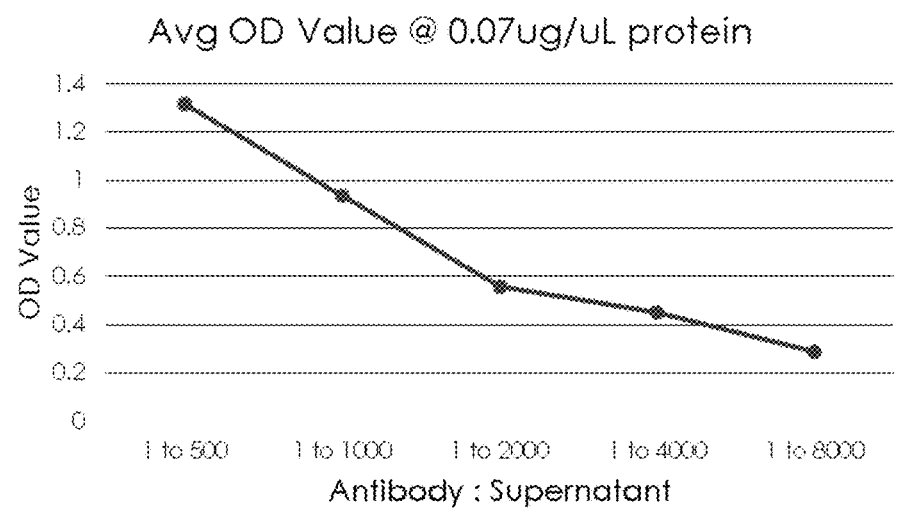
FIG. 7. Detection of diagnostic biomarker RC0497 using monoclonal antibody Clone 7F by ELISA.
Figure 8:
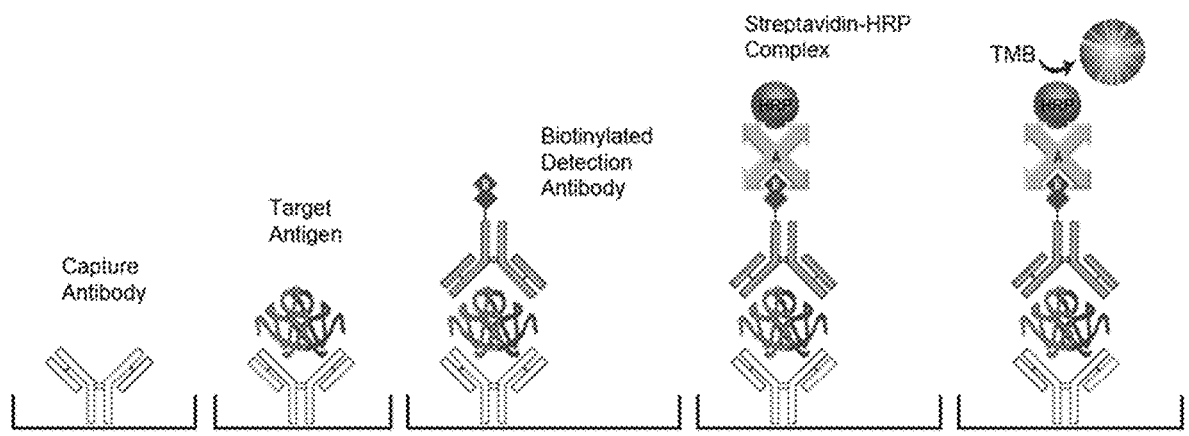
FIG. 8. The schematic Sandwich ELISA for spotted fever rickettsioses. The target antigen will be RC0497.

Identification of protein panel that differentiates lethal disease (LD) vs SLD. The top 5 informative markers are shown in Table 2. The abundance of the proteins are plotted in FIG. 6. Spotted fever group (SFG) rickettsiae are considered as the important tick-borne pathogens causing diseases prevalent throughout the world. Among spotted fever rickettsioses, Rocky Mountain spotted fever (RMSF, caused by *Rickettsia rickettsii*) and Mediterranean spotted fever (MSF, caused by *Rickettsia conorii*) are the most severe diseases with fatality rates as high as 40% if not treated promptly with appropriate antibiotics. RMSF has been recently reported to occur in Arizona as well as Central and South America. MSF is prevalent throughout the southern Europe, northern Africa, the Middle East, and central Asia. Patients with spotted fever rickettsioses usually present with fever, headache, and rash. Severe cases develop interstitial pneumonia, meningoencephalitis, and multi-organ failure.

A panel of polyclonal and monoclonal antibodies directed against RC0497 have been developed. More importantly, these antibodies are able to specifically bind RC0497 by both immunoblotting and ELISA. Recombinant RC0497 was plated as the antigen at the concentration of 0.07 µg/µl. One of the monoclonal antibody clones (7F) was used at different concentrations to detect RC0497. No significant signal was detected in the negative controls. These results demonstrate the feasibility of detecting the diagnostic biomarker RC0497 using immunoassay.

Certain aspects are directed to a sandwich ELISA to detect RC0497 in the serum of patients at the acute stage of spotted fever rickettsioses using a time- and cost-efficient strategy. In brief, the optimal mouse monoclonal antibody against RC0497 will be used as the capture antibody after coating the plate. After blocking, patient serum, which contains RC0497 or its fragments, will be added to bind to the capture antibody. Purified rabbit polyclonal antibody against RC0497 will be biotinylated and used as the detection antibody. The antigen, RC0497, will be bound between these two layers of antibodies. The ultraAvidin-HRP conjugate will be added prior to TMB substrate solution. The enzyme-substrate reaction can be used as the detection signal. The capture and detection antibodies must be chosen to prevent cross-reactivity or competition of binding sites. The specificity and sensitivity can be measured using serum samples from healthy individuals and infected patients.

In an aspect, the invention provides a method of detecting one or more biomarker (e.g., RC0497 or a fragment thereof) in a biological sample comprising: (a) contacting a biological sample with a reagent designed to determine a presence or level of the one or more biomarker, wherein the one or more biomarker is selected from the RC0497 or a fragment thereof; and (b) identifying the one or more biomarkers in the biological sample, thereby detecting the one or more biomarker in the biological sample.

Biomarkers. A biomarker, such as the RC0497 protein or fragments thereof, is a biomolecule that is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for disease (diagnostics), therapeutic effectiveness of a drug (theranostics) and of drug toxicity.

The current invention seeks to develop method for identifying patients having *rickettsia* infection based on multiple factors including clinical features, biochemical assays, and expression profiling.

Assays. In certain aspects, the biomarkers of this invention can be measured or detected by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies.

Embodiments described herein contemplate traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

Kits. In another aspect, the present invention provides kits for qualifying *rickettsia* status, which kits are used to detect biomarkers described herein. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecific capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

Examples. The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 9:
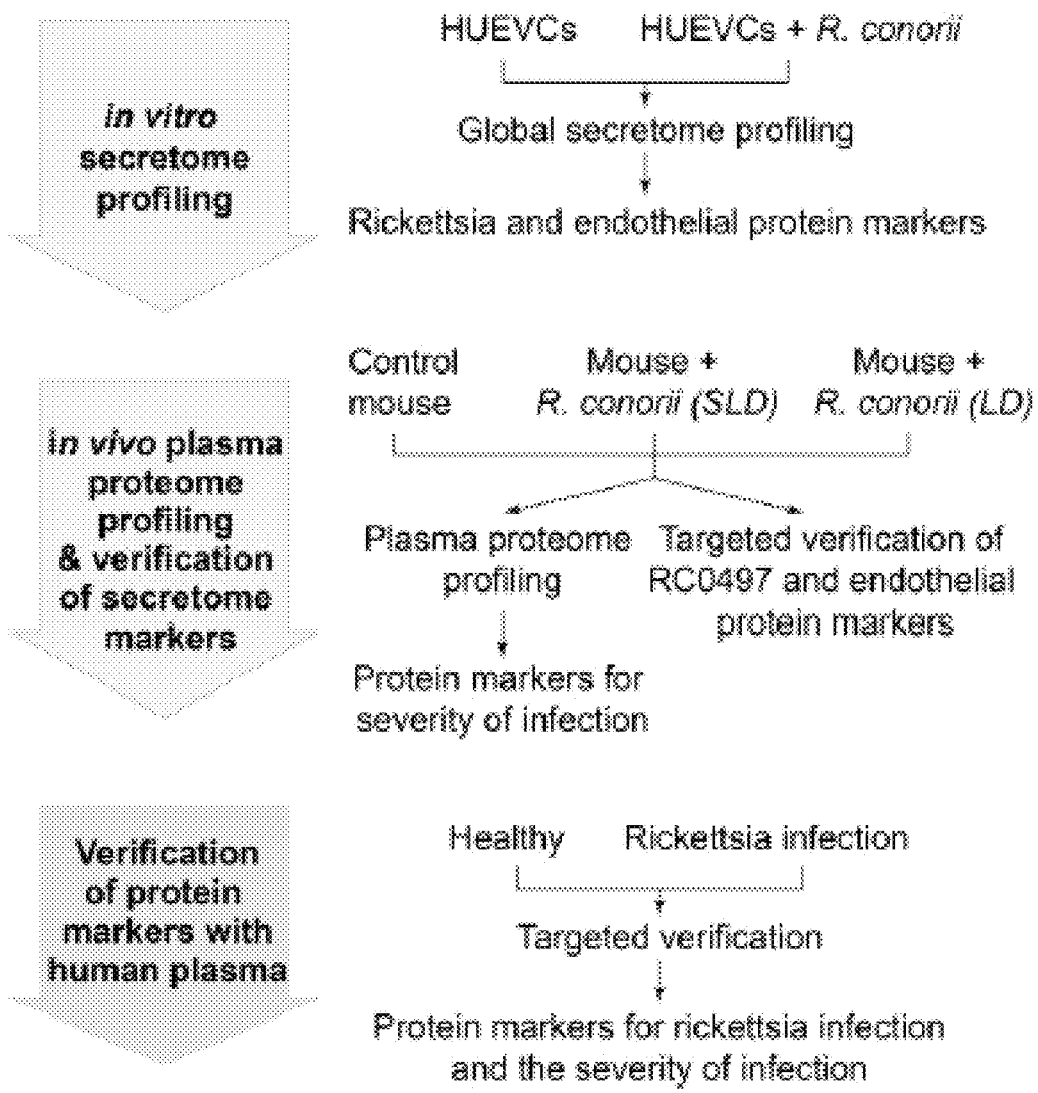
FIG. 9. Workflow of identification of the biomarkers for rickettsial infection and the severity of infection. The biomarker development workflow has three steps. In step 1, the potential protein markers for R. conorii infection were identified via proteomics profiling of the secretome of HUVECs infected with R. conorii. In step 2, the presence of the secretome markers in the plasma were verified using a mouse model of rickettsial infection, and the potential markers for the severity of rickettsia infection were identified via proteomics profiling of the plasma from the animals with different doses of R. conorii. SLD, sub-lethal dose; LD, lethal dose. In step 3, the protein markers identified in the steps 1 and 2 were verified using the plasma from patients with rickettsia infection.

Quantitative Proteomics of the Endothelial Secretome Identifies RC0497 as Diagnostic Biomarker of Acute Spotted Fever Rickettsioses A major challenge in the development of rickettsial diagnostics is that the infection is localized to the vascular endothelium, and bacteremia is not typically present. To circumvent this limitation, markers for early *R. conorii* infection are identified (FIG. 9). First, the focus was on the analysis of the dynamic changes in the endothelial secretome in response to *R. conorii* infection. The secretome of primary human umbilical vein endothelial cells (HUVECs) infected with *R. conorii* were profiled. With this approach, the putative N-acetylmuramoyl-L-alanine amidase RC0497 was identified as the most abundant rickettsial protein in *R. conorii*-infected HUVEC-conditioned medium and a highly specific candidate for a diagnosis of rickettsial infection. Next, proteomics studies of plasma from mice infected with either sub-lethal or lethal doses of *R. conorii* were conducted, and a cluster of increased amounts of acute phase reactants and coagulation factors were identified. As expected, no rickettsial proteins were detected in this discovery study, confirming the low abundance of bacterial proteins in the circulation. To increase the sensitivity of detection, a stable isotope dilution (SID)-parallel reaction monitoring (PRM) assay was developed to detect RC0497 in plasma of infected animals and found that its circulating levels are proportional to the bacterial burden. Finally, an immunoprecipitation (IP) enrichment-SRM assay was developed to detect the low abundance of circulating RC0497 and validated this assay as a diagnostic approach in a cohort of humans presenting with acute rickettsial infections. Because RC0497 is conserved in more than ten species of the rickettsial spotted fever group, its detection is a specific marker for diagnosis of acute infection. This assay will also advance the epidemiological studies of this infection.

A. Materials and Methods

Reagents. All reagents and solvents in LC-MS/MS analyses were ACS grade. Ammonium bicarbonate (ABC), 2,2,2,-trifluoroethanol (TFE), and acetic acid were purchased from Sigma-Aldrich. Iodoacetamide (IDA), dithiothreitol (DTT), acetonitrile (ACN), formic acid, and methanol were purchased from Thermo Scientific (Waltham, MA, USA). Urea ultra was from MP Biomedicals (Santa Ana, CA, USA). Sequencing-grade modified trypsin and LysC were from Promega (Madison, WI, USA). Recombinant rickettsial putative N-acetylmuramoyl-L-alanine amidase RC0497 was purchased from MyBiosource (San Diego, CA).

*Rickettsia*. *R. conorii* (Israeli spotted fever strain, ISF) was obtained from the American Type Culture Collection (ATCC; Manassas, VA). For in vitro cell infection, *R. conorii* ISF strain was cultivated in Vero cells. To purify rickettsiae, cells were homogenized, and rickettsiae were diluted in a 10% suspension of sucrose-phosphate-glutamate (SPG) buffer (0.218 mM sucrose, 3.8 mM $KH_2PO_4$, 7.2 mM $K_2HPO_4$, 4.9 mM mono-sodium glutamic acid, pH 7.0) and stored at −80° C. For mouse inoculation, *R. conorii* (Malish 7 strain) was obtained from the American Type Culture Collection (ATCC; Manassas, Va.; catalog no. VR-613). Rickettsiae were propagated in the yolk sacs of specific-pathogen-free embryonated chicken eggs. The concentrations of stock rickettsiae cultured in both yolk sacs and cell culture were determined by plaque assay. The rickettsial stock was stored at −80° C. until used, and all the experiments described in this study were performed in a certified biosafety level 3 (BSL3) laboratory at the University of Texas Medical Branch at Galveston (UTMB).

Ethical approval. Animal experiments were performed according to the NIH Guide for Care and Use of Experimental Animals and approved by the University of Texas Medical Branch (UTMB) Animal Care and Use Committee (IACUC No. 90-07082). This study of human subjects was conducted under approval from the UTMB Institutional Review Board (No. 08-258), and was compliant with all applicable federal regulations governing the protection of human subjects.

Cell Cultures. Pools of HUVECs were established from individual human umbilical cords grown in supplemented EGM-Plus endothelial cell growth medium (Lonza, catalog no. CC-5035) without the addition of GA-1000 (gentamicin sulfate and amphotericin-B) or fetal bovine serum. The cells were subcultured when the monolayer became confluent. In this study, the cells were used between passages 3 and 4. For infection, $15\times10^6$ primary HUVECs in T175 flasks were infected in BSL-3 containment, and subsequently the conditioned medium was collected 24 h post infection. The conditioned medium was filtered through a 0.22 µm membrane filter to remove infectious rickettsiae in accordance with approved protocols.

Trypsin digestion of the secretome of HUVECs infected with *R. conorii*. The isolation of secretome was performed. Briefly, the conditioned medium was collected and centrifuged at 2000×g at 4° C. for 20 min to remove any dead cells. The supernatant was centrifuged at 10,000×g at 4° C. for 10 min to remove cell debris. The supernatant was further concentrated using Amicon ultra-4 centrifugal filters-3K (Millipore, Billerica, MA, USA). Then 200 µL of 8 M urea was added into centrifugal filters to denature the proteins. Next, the proteins were reduced with 10 mM dithiothreitol (DTT) for 30 min, followed by alkylation with 30 mM iodoacetamide for 60 min at room temperature in the dark. The centrifugal filters were centrifuged at 14,000×g at 4° C. for 15 min, and 200 µL of 50 mM of ammonium bicarbonate (pH 8.0) was added into the sample. The centrifugal filters were centrifuged at 14,000×g at 4° C. for 15 min again. The sample that remained in the filter was transferred into a 0.5-mL microcentrifugation tube. The proteins were digested with 1.0 µg LysC-trypsin (Promega) for 12 h at 37° C., then diluted, and further digested with 1.0 µg trypsin (Promega) for 16 h at 37° C. The digestion was terminated with 0.5% trifluoroacetic acid. The peptides were desalted on a reversed-phase SepPak C18 cartridge (Waters), and eluted with 80% acetonitrile. The eluate was dried in a SpeedVac and the peptides were resuspended in 2% acetonitrile-0.1% trifluoroacetic acid for LC-MS/MS analysis.

Label-free quantification of protein expression. The desalted peptides were reconstituted in 30 µ4% ACN/0.1% formic acid. All peptide samples were separated on an online nanoflow Easy nLC1000 UHPLC system (Thermo Scientific) and analyzed on a Q Exactive Orbitrap mass spectrometer (Thermo Scientific, San Jose, CA). 10 µl of sample was injected onto a capillary peptide trap column (Acclaim® Pepmap 100, 75 µm×2 cm, C18, 3 µm, 100 Å, Thermo Scientific). After sample injection, the peptides were separated on a 25-cm UHPLC reversed phase column (Acclaim® Pepmap 100, 75 µm×25 cm, C18, 2 µm, 100 Å, Thermo Scientific) at a flowrate of 300 nL/min. A 2-h linear gradient from 2% solvent A (0.1% formic acid in water) to 35% solvent B (0.1% formic acid in acetonitrile) was used for each LC-MS/MS run. Data-dependent acquisition was performed using the Xcalibur 2.3 software in positive ion mode at a spray voltage of 2.1 kV. Survey spectra were acquired in the Orbitrap with a resolution of 70,000, the maximum injection time of 80 ms, an automatic gain control (AGC) of $1\times10^6$, and a mass range from 400 to 1400 m/z. The top 15 ions in each survey scan were selected for higher-energy collisional dissociation (HCD) scans with a resolution of 17,500. For all higher-energy collisional dissociation (HCD) scans, collision energy was set to 30, the maximum inject time was 60 ms and the AGC was $1\times10^5$. Ions selected for MS/MS were dynamically excluded for 30 s after fragmentation.

All data were analyzed with the MaxQuant software (version 1.5.2.8) 20, 21 with the *Andromeda* search engine. The false discovery rate (FDR) was set to 1% for both proteins and peptides, and specified a minimum length of 7 amino acids. The *Andromeda* search engine was used for the MS/MS spectra search against a combined SwissProt human and rickettsial database (downloaded on December 2015 containing 20,193 human protein entries, 4,476 Rickettsial protein entries and 247 contaminants). Enzyme specificity was set as C-terminal to Arg and Lys, also allowing cleavage at proline bonds and a maximum of two missed cleavages. Carbamidomethylation of cysteine was selected as fixed modification and methionine oxidation as variable modifications. The 'match between runs' feature of MaxQuant was used to transfer identifications to other LC-MS/MS runs based on their masses and retention time (maximum deviation 0.7 min), and this was also used in quantification experiments. Quantifications were performed with the label-free algorithms in Maxquant. At least one 'razor peptide' was required for quantification. The Perseus platform was used to analyze the Maxquant output, including statistics, Hierarchical clustering, and principal component analysis (PCA). Reversed identifications and proteins identified only by site modification were strictly excluded from further analysis. After filtering (2 valid values in at least one group), remaining missing values were imputed from a normal distribution (width: 0.3 of standard deviation; down shift: 1.8 of standard deviation). Student's t-test was performed to identify the significantly differentially expressed proteins with a Permutation-based FDR<0.01. The unsupervised hierarchical clustering and heat map were based on protein expression. The rows of the heat map indicate the proteins, and the columns indicate the samples. The log 2 ratios of each protein were z-score normalized for each row. Hierarchical clustering of the z-normalized log 2 ratio was performed using Euclidean distances between means. The number of clusters was set as 300. Genome ontology enrichment analysis of molecular functions and biological function in differentially expressed proteins used Panther (URL pantherdb.org/). This classification uses an evolutionary framework to infer protein functions in a species-independent manner.

Stable Isotope Dilution (SID)-Selected Reaction Monitoring (SRM)-MS validation of differentially expressed secreted proteins. The SID-SRM-MS assays of selected proteins were developed for each targeted protein, two or three peptides were initially selected, and then the sensitivity and selectivity of these were experimentally evaluated. The peptide with best sensitivity and selectivity was selected as the surrogate for that protein. For each peptide, 3-5 SRM transitions were monitored. The peptides were chemically synthesized incorporating isotopically labeled $[^{13}C_6{}^{15}N_4]$ arginine or $[^{13}C_6{}^{15}N_2]$ lysine to a 99% isotopic enrichment (Thermo Scientific, San Jose, CA). The amount of stable isotope labeled standard (SIS) peptides was determined by amino acid analysis. The proteins were trypsin digested on the beads as described above. The tryptic digests were then reconstituted in 30 µl of 5% formic acid-0.01% TFA. An aliquot of 10 µl of 50 fmol/µL diluted SIS peptides was added to each tryptic digest. These samples were desalted with a ZipTip C18 cartridge. The peptides were eluted with 80% ACN and dried. The peptides were reconstituted in 30 µl of 5% formic acid-0.01% TFA and were directly analyzed by liquid chromatography (LC)-SRM-MS. LC-SRM-MS analysis was performed with a TSQ Vantage triple quadrupole mass spectrometer equipped with a nanospray source (Thermo Scientific, San Jose, CA). About 8-10 targeted proteins were analyzed in a single LC-SRM run. The online chromatography was performed using an Eksigent NanoLC-2D HPLC system (AB SCIEX, Dublin, CA). An aliquot of 10 µL of each of the tryptic digests was injected on a C18 reverse-phase nano-HPLC column (PicoFrit™, 75 µm×10 cm; tip ID 15 µm) at a flow rate of 500 nL/min with a 20-min 98% A, followed by a 15-min linear gradient from 2-30% mobile phase B (0.1% formic acid-90% acetonitrile) in mobile phase A (0.1% formic acid). The TSQ Vantage was operated in high-resolution SRM mode with Q1 and Q3 set to 0.2 and 0.7-Da Full-Width Half Maximum (FWHM). All acquisition methods used the following parameters: 2100 V ion spray voltage, a 275° C. ion transferring tube temperature, a collision-activated dissociation pressure at 1.5 mTorr, and the S-lens voltage used the values in S-lens table generated during MS calibration.

All SRM data were manually inspected to ensure peak detection and accurate integration. The chromatographic retention time and the relative product ion intensities of the analyte peptides were compared to those of the stable isotope labeled standard (SIS) peptides. The variation of the retention time between the analyte peptides and their SIS counterparts should be within 0.05 min, and the difference in the relative product ion intensities of the analyte peptides and SIS peptides was below 20%. The peak areas in the extract ion chromatography of the native and SIS version of each signature peptide were integrated using Xcalibur® 2.1. The default values for noise percentage and base-line subtraction window were used. The ratio between the peak area of native and SIS version of each peptide was calculated.

In vivo study. Age- and sex-matched C3H/HeN mice were purchased from Charles River Laboratories (Wilmington, MA). Mice were inoculated intravenously (i.v.) through the tail vein with R. conorii Malish 7 strain with either a sub-lethal dose (SLD) 0.1 LD50 (5×10$^3$ PFU) or a lethal dose (LD) 3LD50 (1.5×10$^5$ PFU) of rickettsiae. Negative controls were inoculated with 300 µl of SPG buffer alone. Mice were monitored daily for signs of illness including ruffled fur, hunched posture, and decreased activity. Mice were sacrificed on day 4 p.i. Mice were anesthetized by inhalational isoflurane (Isoflurane® USP, Piramal Healthcare Limited, 502321 Andhra Pradesh, India) and euthanized by CO$_2$ inhalation followed by cervical dislocation. Whole mouse blood was recovered by cardiac puncture immediately after euthanasia. All animal experiments were conducted in a certified animal biosafety level 3 (ABSL3) laboratory. Experiments in mice were performed according to the guidelines of the Guide for the Care and Use of Laboratory Animals.

Trypsin digestion of mouse plasma or human serum and label free quantification. Ten microliters of plasma were aliquoted from each sample, and 50 µl of 9 M urea was added. The protein concentration was measured by bicinchoninic acid assay. About 200 µg of proteins from each sample were used for protein digestion. The proteins were first reduced with 10 mM DTT at room temperature for 30 min, followed by alkylation with 30 mM iodoacetamine at room temperature for 1 h. Then, the sample was diluted 2× with 50 mM ammonium bicarbonate (pH 8.0). An aliquot of Lys-C/Trypsin solution (Promega, Madison, WI) was added into each sample at a 100:1 protein:enzyme ratio. The samples were incubated at 37° C. overnight, and the solutions were further diluted 5× with 50 µM of ammonium bicarbonate. An aliquot of Trypsin solution (Promega, Madison, WI) was added into each sample at a 50:1 protein:enzyme ratio. The samples were incubated at 37° C. for 16 h. 10 µL of 10% trifluoroacetic acid was added into each sample to stop the trypsin digestion. Tryptic peptides were desalted on reversed phase tC18 SepPak columns (Waters, Milford, MA) and evaporated to dryness in a vacuum concentrator. The peptides were resuspended in 2% acetonitrile-0.1% trifluoroacetic acid and analyzed by LC-MS/MS as described above. The mass spectrometry data were analyzed with MaxQuant software as described above.

Parallel reaction monitoring (PRM) analysis of Rickettsia protein RC0497, An aliquot of stable isotope labeled peptide (SIS) of rickettsial protein RC0497 (LLLSLDSTGEK [$^{13}C_6^{15}N_2$] was added into each sample. For PRM analyses, the acquisition employed an orbitrap resolution of 70,000 (@m/z 200), a target AGC value of 3×10$^6$, and maximum fill times of 200 ms for full scan; 17,500 (@m/z 200), a target AGC value of 2×10$^5$, and maximum fill times of 100 ms for MS2 scan. PRM targeted the pair of peptides of rickettsial protein RC0497 [(native and stable isotope labeled standard (SIS) peptides). All peptide samples were separated on an online nanoflow Easy nLC1000 UHPLC system (Thermo Scientific) and analyzed on an Q Exactive Orbitrap mass spectrometer (Thermo Scientific, San Jose, CA) as described above. The assessment of the detection of peptides was performed post-acquisition using Skyline version 3.6.0.9321. For each peptide under evaluation, the signals of the five most intense fragment ions (as defined in spectra of SIS peptides of RC0497) were extracted from each corresponding MS/MS spectrum. The MS/MS spectra with at least five fragment ions detected were submitted to spectral matching. The comparison of the relative intensities of these fragments with those defined in the reference composite MS/MS spectrum was performed based on dotp value. In addition, the retention time of the native and SIS peptides was used as an additional acceptance criterion. The variation of the retention time between the analyte peptides and their SIS counterparts should be within 0.05 min.

Generation of anti-RC0497 antibodies. Recombinant protein Rc0497 was expressed in E. coli. After expression, the protein was purified using Ni-resin and dialyzed to remove imidazole and benzamidine to optimize thrombin activity followed by removal of His-tag. Rabbit polyclonal antibodies against RC0497 were generated by Rockland Immunochemicals, Inc. (Limerick, PA). The antibodies then underwent either protein A or affinity purification. The reactivity of polyclonal antibody with RC0497 was confirmed by immunoblotting and immunoprecipitation-SRM.

Immunoprecipitation (IP) of RC0497 and trypsin digestion. About 100 µL of serum was suspended in 1 mL of low ionic strength immunoprecipitation buffer (50 mM NaCl, 25 mM HEPES pH 7.4, 1% IGEPAL CA-630, 10% glycerol, 1 mM fresh DTT, and protease inhibitor cocktail). A aliquot of 4 µg of anti-RC0497 antibody or control IgG (Rabbit polyclonal, Santa Cruz) was used in each IP. The mixture was incubated overnight at 4° C.; then, 30 µL of protein A magnetic beads (Dynabeads, Invitrogen) were added. After incubation at 4° C. for 4 h, the beads were separated from the supernatant with a magnetic stand. The beads were washed with PBS five times before trypsin digestion. The trypsin digestion was performed. The beads were suspended with gentle vortexing for 1 h. The proteins on the beads were reduced with 10 mM DTT for 30 min, then alkylated with 20 mM IDA for 1 h in the dark. An aliquot of 4 μg of sequencing-grade trypsin was added to each sample before a 4 h incubation at 37° C. with gentle shaking; the supernatant was then collected. Another 4 μg of trypsin was then added to the beads, and the sample was incubated at 37° C. overnight with gentle shaking; the supernatant was then collected. After trypsin digestion, the beads were washed twice with 50 μL of 50% ACN, and the supernatants were collected. All of the supernatants were combined and dried with a SpeedVac.

B. Results

Figure 10:
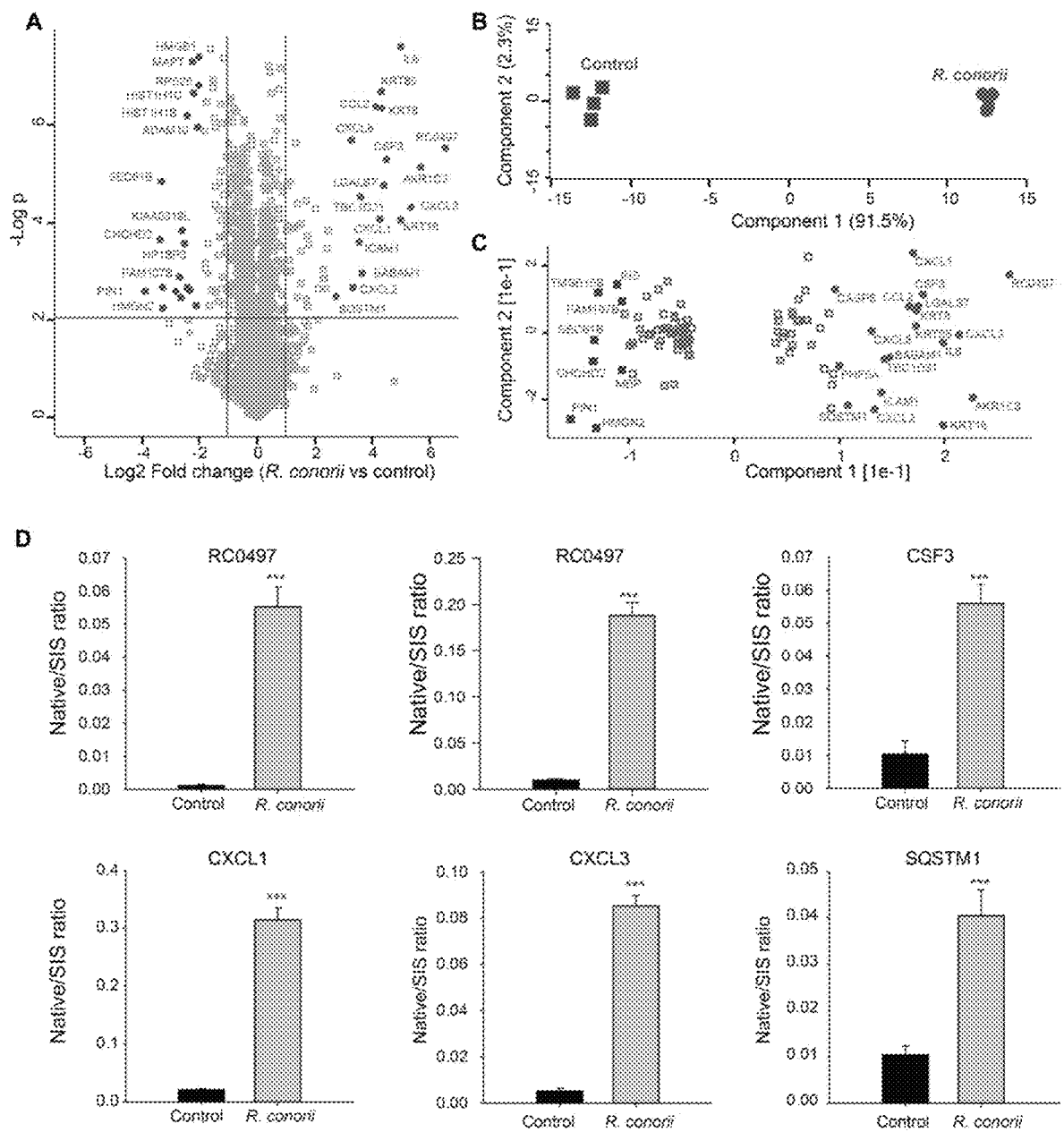
FIG. 10. Quantitative proteomics analysis of the secretome of primary human umbilical vein endothelial cells infected with R. conorii. The HUVECs were infected with R. conorii for 24 h. The cell culture media were collected, and the secretory proteins from HUVECs were analyzed by label-free LC-MS/MS. (A) Volcano plot of protein expression in the secretome of HUVECs infected with R. conorii. The dots above the horizon line are proteins whose levels in the secretome of HUVECs were significantly changed in response to R. conorii infection (Student's t-test, Permutation-based FDR 1%). The vertical lines indicate the 2-fold change cutoff. Some most significantly up- or down-regulated proteins were labeled. (B) Projection of principal component analysis of 104 proteins whose levels in the secretome of HUVECs were significantly changed in response to R. conorii infection (Student's t test with Permutation-based FDR 1% and 2-fold change cutoff). The first two components of data variability of 104 proteins, from four replicates of Control HUVECs (blue squares) and four replicates of R. conorii infected-HUVECs, are shown. (C) Scatter plot depicts the protein feature loadings of 3 component 1 and component 2 of the PCA in FIG. 10B. Protein features showing significant importance in dividing control and rickettsial groups were labeled. (D) SID-SRM-MS validation of differentially expressed proteins. Five proteins that were up-regulated in the HUVECs secretome by R. conorii were selected for further validation with quantitative SID-SRM-MS. RC0497 was measured with two signature peptides. The error bars are the standard error of SRM measurements. , Student's t-test P value<0.05; *, Student t-test P value<0.001.
Figure 16:
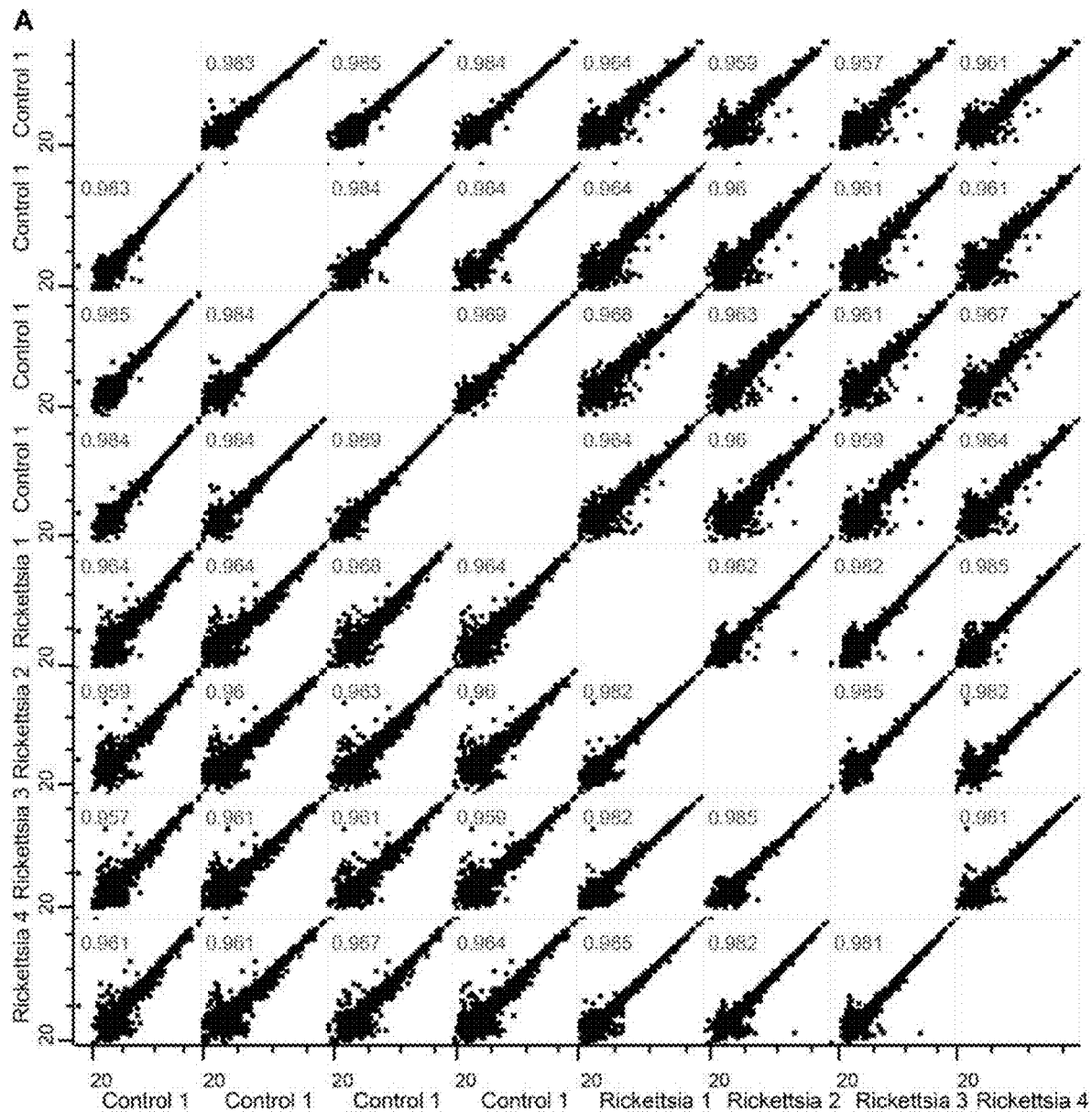
FIG. 16. Multi scatter plots of the proteins intensities between the samples and replicates. The Pearson correlation of the pairwise comparison of protein intensities between samples and replicates was shown in each scatter plot. The value of Pearson correlation of each pair-wise comparison was shown in each scatter plot.

Quantitative proteomics analysis of secretome of HUVECs infected with *R. conorii*. HUVECs are a standardized model for early responses to rickettsial vascular infection. To understand the spectrum of proteins secreted/released by endothelial cells in response to *R. conorii* infection, a quantitative proteomics analysis of the proteins in the conditioned medium of HUVECs with and without *R. conorii* infection were conducted (FIG. 1). 2,655 proteins were identified with 1% false positive rate (FDR). Among them, 2,620 proteins were quantified in all the replicates (Table 4). The intensity of each protein in biological and technical replicates has an excellent agreement (Pearson correlation r>0.95) (FIG. 16), confirming that the MS quantification of proteins was robust and reproducible. Proteins satisfying two criteria—Student's t-test with Permutation-based FDR<0.01 and a two-fold change in the abundance, were considered to be significantly changed by rickettsial infection. With this approach, 104 proteins were identified whose abundance in the conditioned medium was signifi-cantly changed by *R. conorii* infection, including 45 up-regulated and 59 down-regulated proteins. The volcano plot of the logarithm-transformed fold changes in the secretome of HUVECs plotted vs. the Student's t-test p-values is shown in FIG. 10A. Some most significantly up- or down-regulated proteins were highlighted. A principal component analysis (PCA) of the 104 significant proteins confirmed the successful quantitative separation between the *rickettsia*-infected vs control HUVECs (FIG. 10B), indicating that the protein abundances in the conditioned medium are sufficiently informative to discriminate the two groups. Next, the proteins driving the separation (the "loadings" of the multidimensional PCA) were examined to identify the proteins with the highest power to separate the *rickettsia*-infected HUVECs from the control HUVECs. These proteins are highlighted in FIG. 10C and tabulated in Table 3. The proteins on the far right of FIG. 10C includes the rickettsial protein—putative N-acetylmuramoyl-L-alanine amidase RC0497, and human inflammatory cytokines and chemokines (IL6, CXCL1, CXCL2, CXCL3, CXCL8, and CSF3), and the autophagy protein sequestosome-1 (SQSTM1/p62), a protein has been reported to be potentially involved in interactions of rickettsiae with mammalian host cells.

TABLE 3

The proteins with the highest discrimination power between *Rickettsia conorii* -infected HUVECs and control HUVECs. FC, fold change. The abundance levels in the conditioned medium that were significantly changed by *Rickettsia conorii* infection were highlighted in red (elevated) and green (decreased).

| Protein names | Accession # | Gene names | Organism | Log2 FC | −log10 p-value |
|---|---|---|---|---|---|
| Putative N-acetylmuramoyl-L-alanine amidase RC0497 | Q92IC3 | RC0497 | *R. conorii* | 6.54 | 5.51 |
| Aldo-keto reductase family 1 member C3* | P42330 | AKR1C3 | *H. sapiens* | 5.69 | 5.14 |
| C-X-C motif chemokine 3 | P19876 | CXCL3 | *H. sapiens* | 5.34 | 4.30 |
| Keratin, type I cytoskeletal 16 | P08779 | KRT16 | *H. sapiens* | 4.99 | 4.05 |
| Interleukin-6 | P05231 | IL6 | *H. sapiens* | 4.99 | 7.61 |
| Granulocyte colony-stimulating factor | P09919 | CSF3 | *H. sapiens* | 4.47 | 5.29 |
| Galectin-7* | P47929 | LGALS7 | *H. sapiens* | 4.38 | 4.76 |
| Keratin, type II cuticular Hb5 | P78386 | KRT85 | *H. sapiens* | 4.33 | 6.68 |
| Keratin, type II cytoskeletal 8 | P05787 | KRT8 | *H. sapiens* | 4.33 | 6.33 |
| Growth-regulated alpha protein | P09341 | CXCL1 | *H. sapiens* | 4.26 | 4.06 |
| C-C motif chemokine 2 | P13500 | CCL2 | *H. sapiens* | 4.15 | 6.38 |
| BRISC and BRCA1-A complex member 1 | Q9NWV8 | BABAM1 | *H. sapiens* | 3.65 | 2.97 |
| TBC1 domain family member 31 | Q96DN5 | TBC1D31 | *H. sapiens* | 3.60 | 4.52 |
| Intercellular adhesion molecule 1* | P05362 | ICAM1 | *H. sapiens* | 3.54 | 3.58 |
| C-X-C motif chemokine 2 | P19875 | CXCL2 | *H. sapiens* | 3.31 | 2.67 |
| Interleukin-8 | P10145 | CXCL8 | *H. sapiens* | 3.26 | 5.68 |
| Sequestosome-1* | Q13501 | SQSTM1 | *H. sapiens* | 2.72 | 2.48 |
| PHD finger-like domain-containing protein 5A | Q7RTV0 | PHF5A | *H. sapiens* | 2.47 | 3.84 |
| Caspase-6 | P55212 | CASP6 | *H. sapiens* | 2.40 | 3.47 |
| Myelin basic protein | P02686 | MBP | *H. sapiens* | −2.65 | 2.44 |
| Protein FAM107B | Q9H098 | FAM107B | *H. sapiens* | −2.70 | 2.88 |
| Insulin* | P01308 | INS | *H. sapiens* | −2.81 | 2.58 |
| Thymosin beta-15B | P0CG35 | TMSB15B | *H. sapiens* | −3.27 | 2.65 |
| Non-histone chromosomal protein HMG-17 | P05204 | HMGN2 | *H. sapiens* | −3.29 | 2.25 |
| Protein transport protein Sec61 subunit beta | P60468 | SEC61B | *H. sapiens* | −3.34 | 4.85 |
| Coiled-coil-helix-coiled-coil-helix domain-containing protein 2, mitochondrial | Q9Y6H1 | CHCHD2 | *H. sapiens* | −3.36 | 3.65 |
| Peptidyl-prolyl cis-trans isomerase NIMA-interacting 1 | Q13526 | PIN1 | *H. sapiens* | −3.89 | 2.60 |

The changes in the abundance of these proteins in the secretome of HUVECs were further validated with independent quantitative stable isotope dilution (SID)-selected reaction monitoring (SRM)-MS, a "targeted" MS approach for the detection and accurate quantification of proteins in a complex background. SID-SRM-MS provides structural specificity and, therefore, is the most accurate approach available for direct quantification of target proteins in a complex mixture. SRM assays were developed for the measurement of five proteins—RC0497, CSF3, CXCL1, CXCL3, and SQSTM1. Using two proteotypic peptides (SDFPAEQIGK (SEQ ID NO:5) and LLLSLDSTGEK (SEQ ID NO:3)), a marked increase of RC0497 abundance was observed in the conditioned medium of R. conorii-infected HUVECs (FIG. 10D). Similarly, SID-SRM-MS assays confirmed the elevated secretion of CSF3, CXCL-1/-3, and SQSTM1 in response to R. conorii infection (FIG. 10D).

Figure 11:
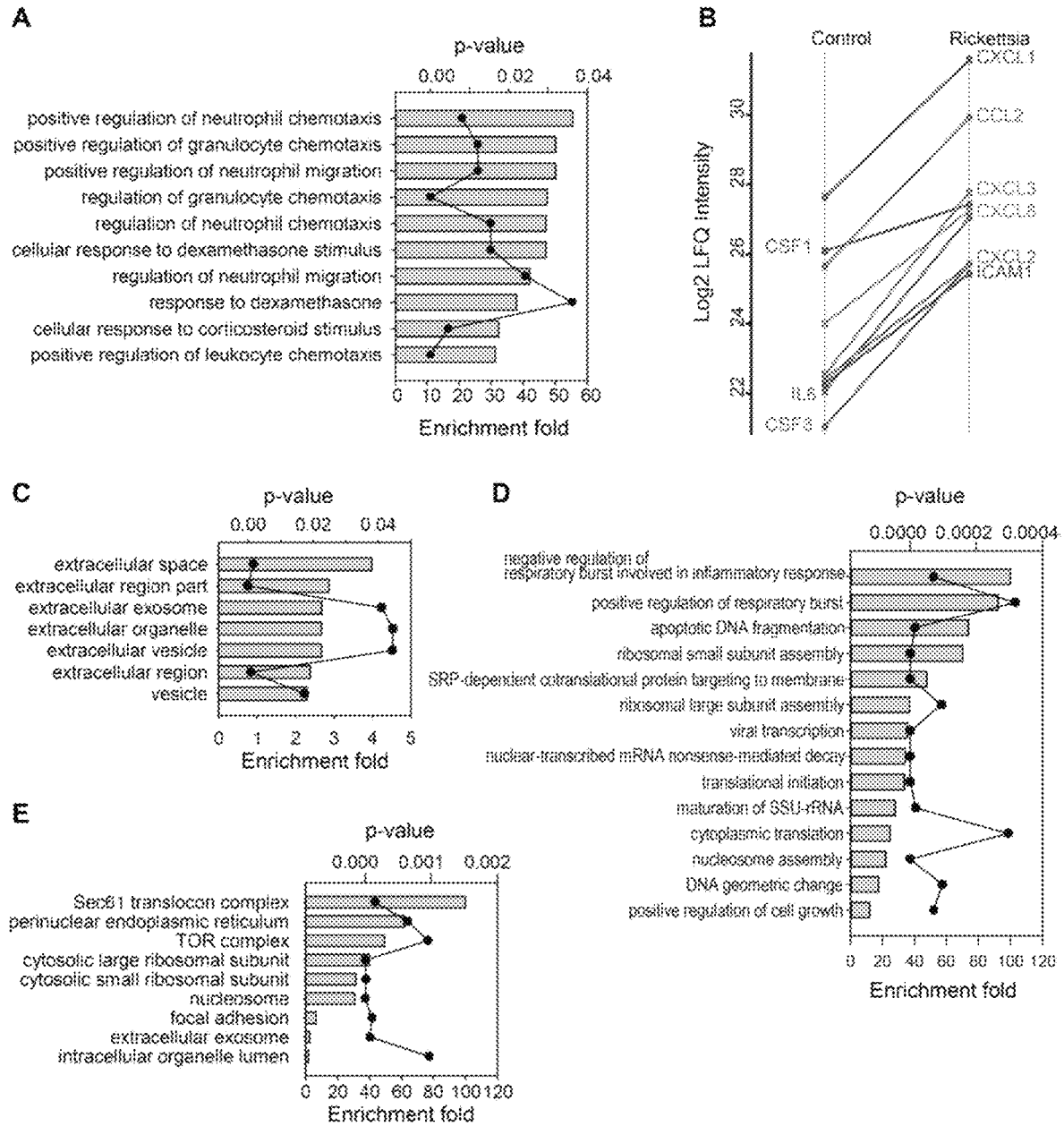
FIG. 11. GO annotation enrichment analysis of differentially expressed secretory proteins. (A) GO biological process enrichment analysis of 45 up-regulated secretory proteins. Bars represent fold enrichment of GO annotation; Scatter-line plot represents the p-value of enrichment analysis. (B) Expression of proteins that are involved in the inflammatory response. (C) GO cellular component enrichment analysis of 45 up-regulated secretory proteins. (D) GO biological function enrichment analysis of 59 down-regulated secretory proteins. (E) GO cellular component enrichment analysis of 59 down-regulated secretory proteins.

Host responses to R. conorii infection. The genome ontology (GO) biological process enrichment analysis of the 45 up-regulated human proteins found that these proteins are involved in positive regulation of neutrophil chemotaxis, chemokine-mediated signaling pathways, and inflammation response (FIG. 11A). Within this group, the secretion of IL6, CXCL1/2/3/8, CCL2, CSF1/3, and intercellular adhesion molecule 1 (ICAM1) were dramatically induced by R. conorii infection (FIG. 11B). The GO cellular component analysis of these 45 proteins shows that the extracellular space proteins were highly enriched, suggesting that these proteins are within the secretory pathway (FIG. 11C). More than half of 45 proteins are identified as extracellular space proteins. Most cytokines and chemokines have $NH_2$-terminal signal peptides and are secreted through classic secretory pathways. By contrast, it is noted that some proteins such as SQSTM1 and aldo-keto reductase family 1 member C3 (AKR1C3) lack signal peptides and are known to be secreted via exosomes, a typical cellular response to stress-autophagy. By contrast, the GO biological process enrichment analysis of the 59 down-regulated proteins found that these proteins were highly enriched for negative regulation of respiratory burst involved in inflammatory response, apoptotic DNA fragmentation and ribosomal small subunit assembly (FIG. 11D). The majority of down-regulated proteins (50 out 59) are organelle proteins. GO cellular component analysis of these 59 proteins shows that Sec61 translocon complex, perinuclear endoplasmic reticulum, and TOR complex are highly enriched (FIG. 11E). According to ExoCarte, a web-based database of exosomal proteins, nineteen out of the 59 proteins are extracellular exosome proteins.

Figure 12:
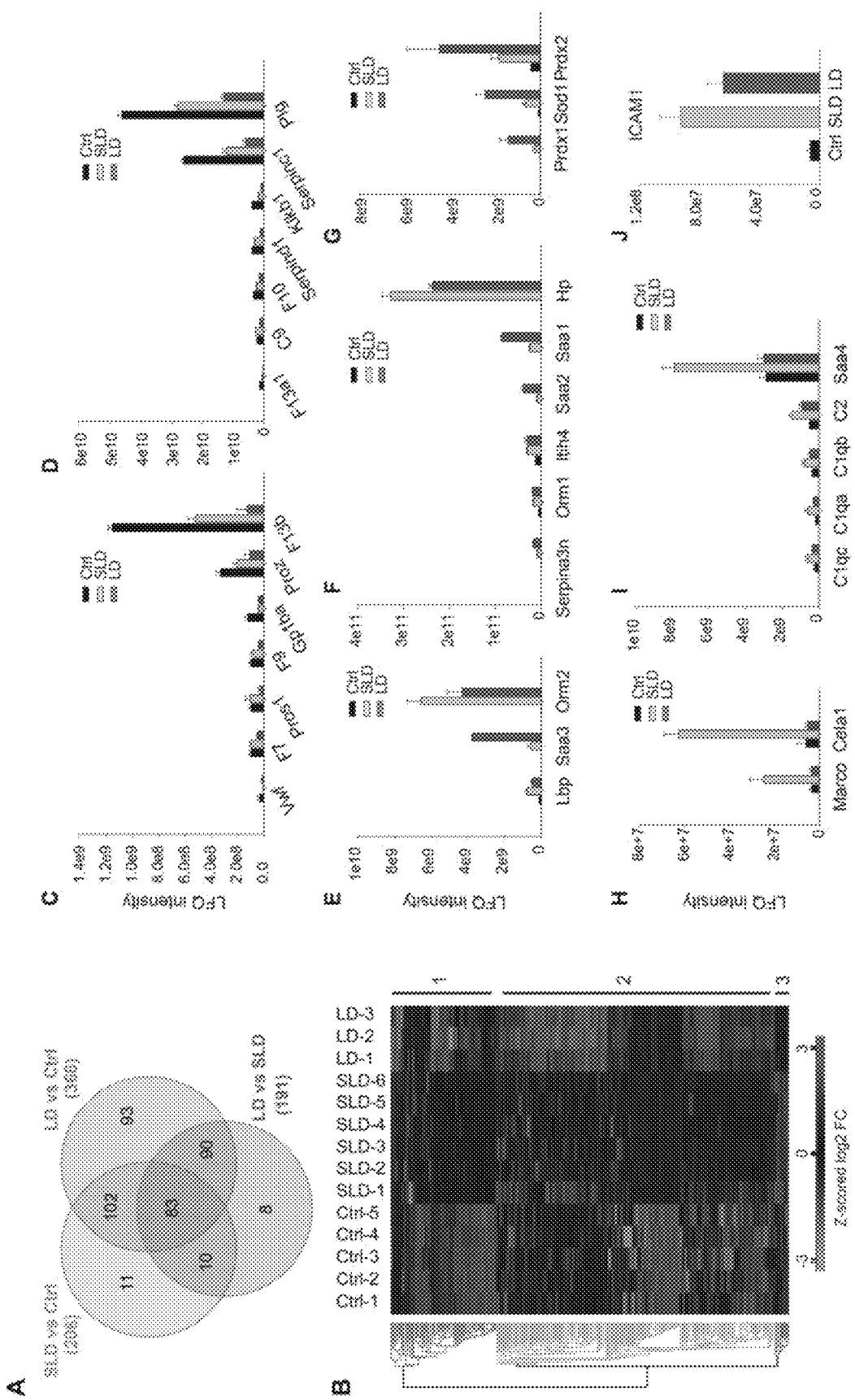
FIG. 12. Differentially expressed serum proteins in response to R. conorii infection. (A) Venn diagram of the overlap of the differentially expressed serum proteins from two pairwise comparisons. SLD, sub-lethal dose (n=6); LD, lethal dose (n=3); and Ctrl, control (n=5). (B) Heatmap of the expression of proteins that were differentially expressed in at least one pairwise comparison. Brown cluster, the proteins were down-regulated after R. conorii infection; Blue cluster, the proteins were up-regulated by R. conorii and more so in mice with lethal dose; purple cluster, the proteins were up-regulated by sub-lethal dose R. conorii. (C) and (D) The expression of proteins involved in blood coagulation. (E) and (F) The expression of proteins involved in the acute response. (G) The expression of proteins involved in the removal of reactive oxygen species. (H) and (I) The expression of proteins involved in the defense response. (J) The abundance of ICAM1 in the plasma.
Figure 17:
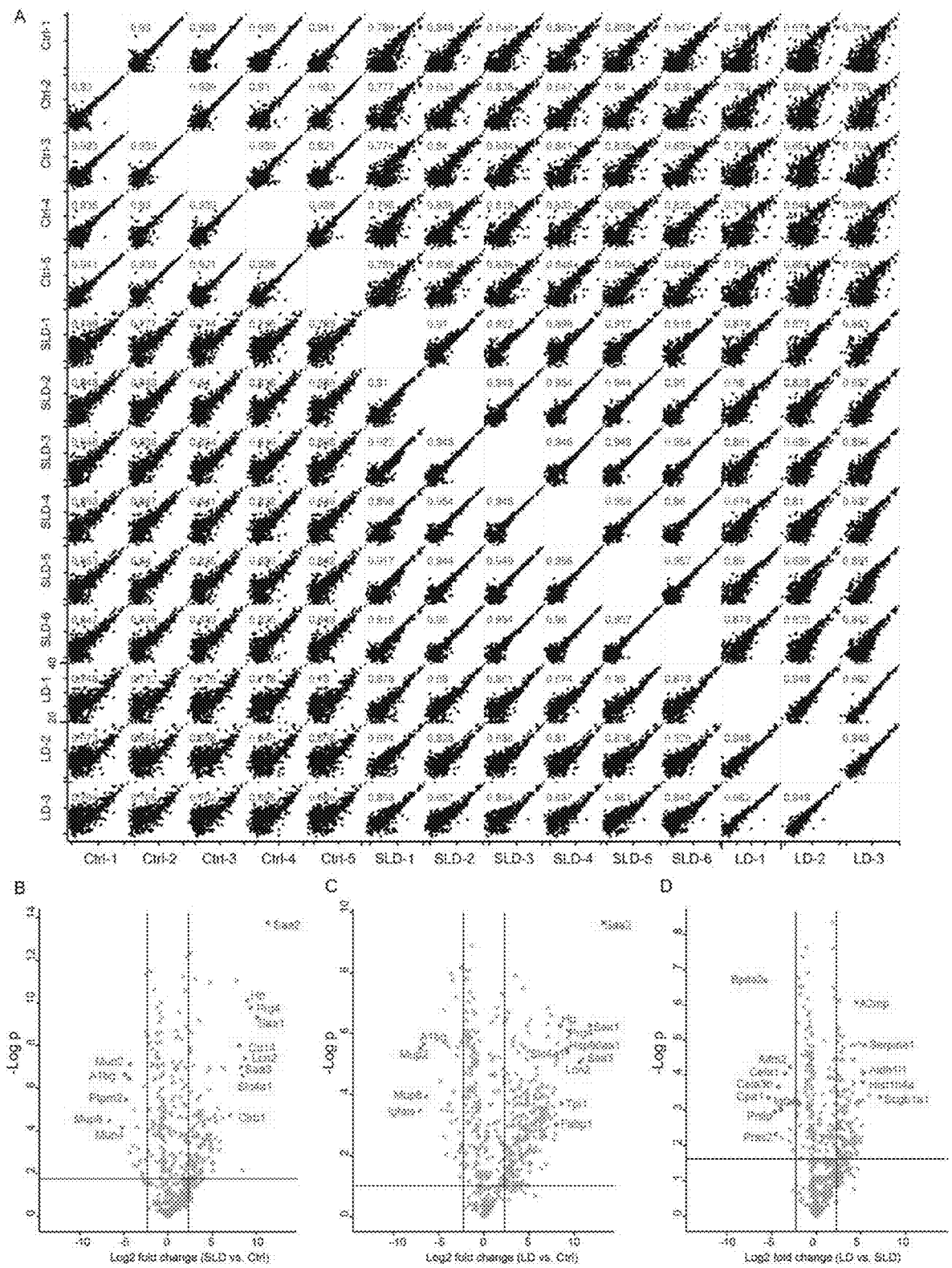
FIG. 17. Quantitative proteomics analysis of the plasma of mice infected with R. conorii. The mice were infected with Rickettsia conorii at two different dose [sub-lethal dose (SLD, n=6) and lethal dose (LD, n=3)]. The mice with infection were used as control (Ctrl, n=5). The mouse plasma proteins were analyzed by label-free LC-MS/MS. (A) Multi scatter plots of the proteins intensities between the samples and replicates. The Pearson correlation of the pairwise comparison of protein intensities between samples and replicates was shown in each scatter plot. (B) Volcano plot of the comparison of protein expression between SLD and Ctrl. (C) Volcano plot of the comparison of protein expression between LD and Ctrl. (D) Volcano plot of the comparison of protein expression between LD and SLD. The dots above the horizon line are proteins which abundance was significantly changed in response to Rickettsia conorii infection (Student's t-test, Permutation-based FDR 1%). The vertical lines indicate the 2-fold change cutoff. Some most significantly up- or down-regulated proteins were labeled.

Quantitative proteomics analysis of the plasma from mice infected with R. conorii. To identify proteins induced in a small animal model of rickettsial infection, mice were infected with a sub-lethal dose (SLD, n=6) or lethal dose (LD, n=3) of R. conorii; uninfected animals were used as control (Ctrl, n=5). Label-free LC-MS/MS analysis of the mouse plasma identified 608 proteins with 1% FDR. Of these, 534 proteins were quantified in all the samples (Table 4). Comparing the intensity of each protein in biological and technical replicates shows an excellent agreement (Pearson correlation r=0.90-0.96) (FIG. 17A), confirming that the reproducibility of the quantification was excellent and robust. To identify the plasma proteins that indicate rickettsial infection or the severity of the disease, three pair-wise comparisons were performed—SLD vs. Ctrl, LD vs. Ctrl, and SLD vs. LD. Two criteria were used, Student's t-test with Permutation-based FDR 0.01 and two-fold change in the abundance, to determine the significant hits in each pair-wise comparison (FIG. 17B-D). 206, 368, and 191 proteins were identified that met both criteria from each pair-wise comparison, respectively. The overlaps of the significant proteins identified from three pair-wise comparisons are shown in the Venn diagram (FIG. 12A). Overall, a total of 397 significant proteins were identified in the three pair-wise comparisons.

TABLE 4

The host proteins with the highest discrimination power between controls, sub-lethal dose- and lethal-dose Rickettsia conorii infection. Three experimental groups: sub-lethal dose (SLD, n = 6), lethal-dose (LD, n = 3), and control (n = 5). The abundance levels in the plasma that were significantly changed by Rickettsia conorii infection were highlighted in red (elevated) and green (decreased). FC, fold change.

| Protein names | Accession # | Gene names | Log2 FC | −log10 p-value |
|---|---|---|---|---|
| SLD vs Control | | | | |
| Serum amyloid A-2 protein | P05367 | Saa2 | 11.26 | 13.76 |
| Serum amyloid A-1 protein | P05366 | Saa1 | 10.02 | 9.34 |
| Proteoglycan 4 | Q9JM99 | Prg4 | 9.35 | 9.77 |
| Haptoglobin | Q61646 | Hp | 8.97 | 10.12 |
| Neutrophil gelatinase-associated lipocalin | P11672 | Lcn2 | 8.70 | 7.38 |
| Band 3 anion transport protein | P04919 | Slc4a1 | 8.42 | 6.59 |
| Serum amyloid A-3 protein | P04918 | Saa3 | 8.22 | 7.00 |
| Monocyte differentiation antigen CD14 | P10810 | Cd14 | 8.04 | 8.00 |
| Alpha-1-acid glycoprotein 2 | P07361 | Orm2 | 7.75 | 11.05 |
| Chymotrypsinogen B | Q9CR35 | Ctrb1 | 7.05 | 4.76 |
| Glycosylation-dependent cell adhesion molecule 1 | Q02596 | Glycam1 | −3.97 | 3.31 |
| Major urinary protein 2 | P11589 | Mup2 | −4.33 | 7.12 |
| Thrombospondin-1 | P35441 | Thbs1 | −4.41 | 2.99 |
| Alpha-1B-glycoprotein | Q19LI2 | A1bg | −4.43 | 6.46 |
| Receptor-type tyrosine-protein phosphatase N2 | P80560 | Ptprn2 | −4.77 | 5.47 |
| Major urinary protein 4 | P11590 | Mup4 | −5.20 | 4.17 |
| Major urinary proteins 11 and 8 | P04938 | Mup8 | −6.70 | 4.49 |
| LD vs. Control | | | | |
| Serum amyloid A-2 protein | P05367 | Saa2 | 13.28 | 9.65 |
| Serum amyloid A-1 protein | P05366 | Saa1 | 11.79 | 6.29 |
| Serum amyloid A-3 protein | P04918 | Saa3 | 10.91 | 5.15 |
| Neutrophil gelatinase-associated lipocalin | P11672 | Lcn2 | 10.56 | 5.05 |
| Proteoglycan 4 | Q9JM99 | Prg4 | 9.29 | 6.11 |
| Argininosuccinate synthase | P16460 | Ass1 | 9.29 | 5.88 |
| Band 3 anion transport protein | P04919 | Slc4a1 | 9.25 | 5.40 |
| Heat shock protein HSP 90-alpha | P07901 | Hsp90aa1 | 9.15 | 5.51 |
| Triosephosphate isomerase | P17751 | Tpi1 | 8.60 | 3.71 |

TABLE 4-continued

Figure 18:
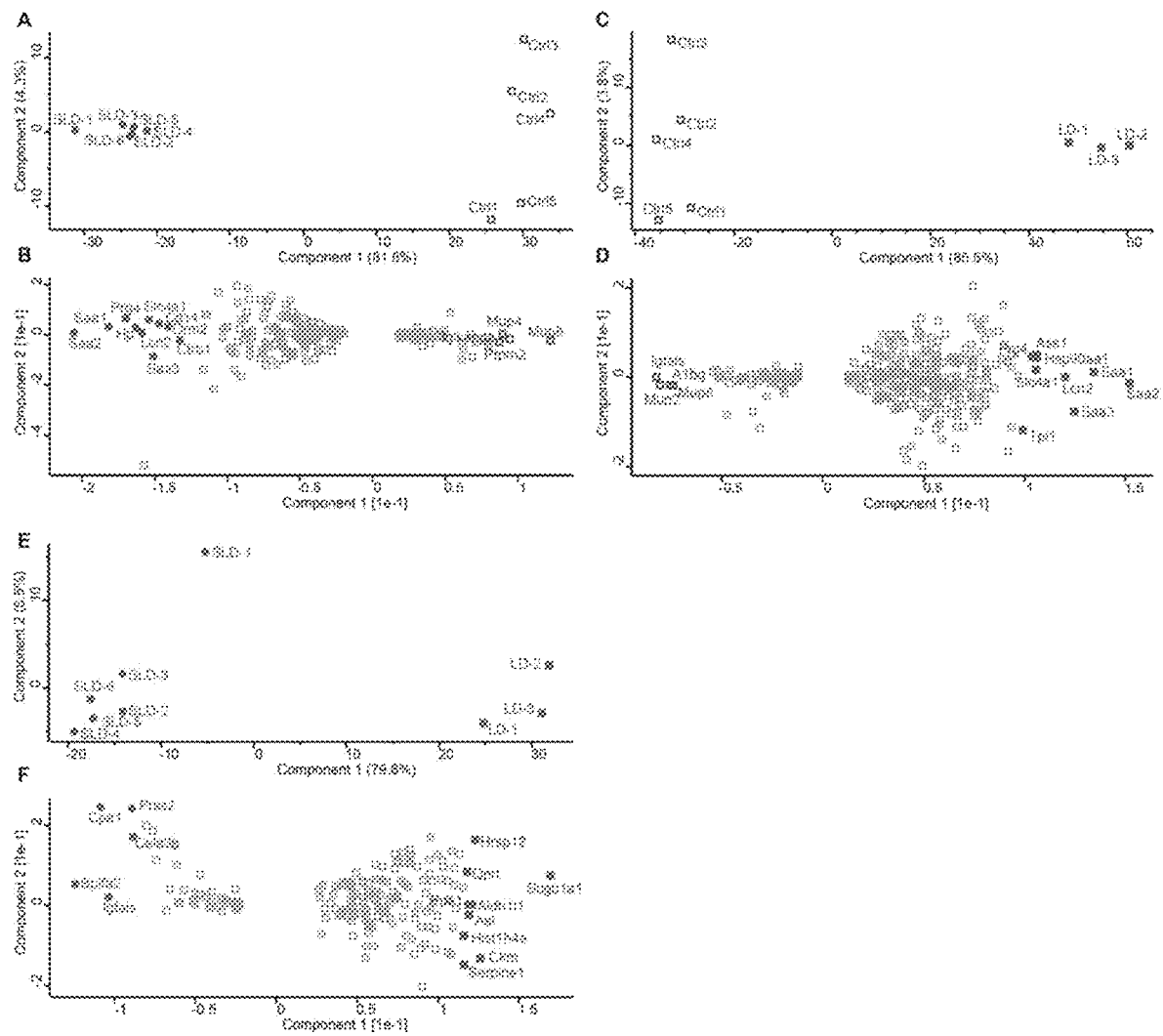
FIG. 18. Principal component analysis. (A) PCA analysis of plasma proteins that were significantly changed by SLD R. conorii infection. Red solid circles are individual animals with SLD R. conorii infection. Uninfected animals (controls) are in blue. (B) Loading plot of the variables (proteins) that lead to the group clustering shown in FIG. S3A. Red proteins are increased by R. conorii infection, green proteins are decreased. (C) PCA analysis of plasma proteins that were significantly changed by LD R. conorii infection. Green squares are individual animals with LD R. conorii infection. Uninfected animals (controls) are in blue. (D) Loading plot of the variables (proteins) that lead to the group clustering shown in FIG. S3C. Green proteins are increased by LD R. conorii infection, blue proteins are decreased. (E) PCA analysis of plasma proteins that were significantly changed by different dose of R. conorii infection. Green squares are individual animals with LD R. conorii infection. Red solid circles are animals with SLD R. conorii infection. (F) Loading plot of the variables (proteins) that lead to the group clustering shown in FIG. S3E. Green proteins are increased by LD R. conorii infection, red proteins are decreased.

The host proteins with the highest discrimination power between controls, sub-lethal dose- and lethal-dose *Rickettsia conorii* infection. Three experimental groups: sub-lethal dose (SLD, n = 6), lethal-dose (LD, n = 3), and control (n = 5). The abundance levels in the plasma that were significantly changed by *Rickettsia conorii* infection were highlighted in red (elevated) and green (decreased). FC, fold change.

| Protein names | Accession # | Gene names | Log2 FC | −log10 p-value |
|---|---|---|---|---|
| Major urinary proteins 11 and 8 | P04938 | Mup8 | −6.42 | 3.93 |
| Alpha-1B-glycoprotein | Q19LI2 | A1bg | −6.63 | 5.65 |
| Major urinary protein 2 | P11589 | Mup2 | −7.00 | 5.52 |
| Insulin-like growth factor-binding protein complex acid labile subunit | P70389 | Igfals | −7.12 | 3.47 |
| LD vs. SLD | | | | |
| Uteroglobin | Q06318 | Scgb1a1 | 7.19 | 3.38 |
| Creatine kinase M-type | P07310 | Ckm | 5.91 | 3.43 |
| Plasminogen activator inhibitor 1 | P22777 | Serpine1 | 5.43 | 4.84 |
| Cytosolic 10-formyltetrahydrofolate dehydrogenase | Q8R0Y6 | Aldh1l1 | 5.37 | 4.03 |
| Histone H4 | P62806 | Hist1h4a | 5.26 | 3.80 |
| Argininosuccinate lyase | Q91YI0 | Asl | 5.22 | 3.28 |
| Inorganic pyrophosphatase | Q9D819 | Ppa1 | 5.18 | 4.12 |
| Adenylyl cyclase-associated protein 1 | P40124 | Cap1 | 5.17 | 2.56 |
| Estradiol 17 beta-dehydrogenase 5 | P70694 | Akr1c6 | 5.03 | 2.23 |
| Nicotinate-nucleotide pyrophosphorylase [carboxylating] | Q91X91 | Qprt | 5.01 | 3.24 |
| Ribonuclease UK114 | P52760 | Hrsp12 | 5.01 | 2.10 |
| Tubulin beta-4B chain | P68372 | Tubb4b | 4.93 | 4.91 |
| Chymotrypsin-like elastase family member 3B | Q9CQ52 | Cela3b | −4.30 | 3.67 |
| Anionic trypsin-2 | P07146 | Prss2 | −4.55 | 2.33 |
| Insulin-like growth factor-binding protein complex acid labile subunit | P70389 | Igfals | −4.68 | 2.96 |
| Carboxypeptidase A1 | Q7TPZ8 | Cpa1 | −5.38 | 3.35 |
| PI fold-containing family A member 2 | P07743 | Bpifa2 | −5.67 | 6.69 |

Unsupervised hierarchical clustering of these 397 proteins identified three clusters (FIG. 12B). The first cluster (dendrogram in FIG. 12B) represents proteins whose abundance in plasma was reduced by the rickettsial infection. The GO biological process enrichment analysis of the proteins in this cluster over the reference human proteome found that the proteins are involved in the removal of high-density lipoprotein particle, alternative complement pathway, fibrinolysis, and blood coagulation. FIGS. 12C and 12D show the abundances of the proteins that regulate blood coagulation, including plasminogen (PLG), coagulation factors (F7, F9, F10, F13A1, and F13B), and von Willebrand factor (VWF). These proteins were depleted from the plasma in response to the *R. conorii* infection, and the magnitude of depletion correlated with infection severity. The second cluster (dendrogram in FIG. 12B) identifies plasma proteins up-regulated by *R. conorii* infection, more significantly in the animals treated with a LD of *R. conorii*. The GO biological process enrichment analysis of the proteins in this cluster determined that proteins involved in the removal of superoxide radicals, gluconeogenesis, and acute-phase response were highly enriched. FIGS. 12E and 12F show the abundances of the proteins that mediate the acute-phase response. Many of these acute phase proteins such as haptoglobin (HP), serum amyloid A-1,2,3 (SAA1/2/3), alpha-1-acid glycoprotein 1 and 2 (ORM1/2), and inter-alpha-trypsin inhibitor heavy chain H4 (ITIH4) are expressed by the liver and secreted into plasma, suggesting that *R. conorii* infection induced a robust hepatic acute phase response. It was also found that superoxide dismutase [Cu—Zn] and peroxiredoxin (PRDX)-1, and 2 were up-regulated in the plasma of infected animals, indicating that the host response to *R. conorii* infection involves antioxidant pathways (FIG. 12G). The third cluster (dendrogram in FIG. 12B) has plasma proteins that were up-regulated more significantly by the SLD of *R. conorii* in comparison to the LD infection. The GO biological function enrichment analysis showed that host defense proteins were highly enriched in this cluster. The proteins belong to this category including macrophage receptor Marco, chymotrypsin-like elastase family member 1 (Cela1) (FIG. 12H), and components of the classical pathway of complement systems (such as C1QA, C1QB, C1QC, AND C2, FIG. 12I). ICAM1, a marker that was identified in the secretome of *R. conorii*-infected HUVEC, was elevated in the plasma of *R. conorii* infected mice (FIG. 12J), indicating the activation of endothelial cells in response to *R. conorii* infection. Other cytokines markers identified in the secretome of *R. conorii*-infected HUVEC were undetected in the label-free mass spectrometric analysis of mouse plasma, probably because the presence of high-abundance of classic plasma proteins such as albumin and hepatic acute phase proteins hindered the detection of low abundance cytokines by mass spectrometry.

A principal component analysis (PCA) of the 397 significantly changed proteins yielded quantitative separation among the animals in the SLD, LD, and uninfected control groups (FIG. 12A), indicating that the protein abundances in plasma are sufficiently informative to discriminate between these groups. To identify the proteins with the highest power to separate the SLD group from the control group, a PCA analysis of the 206 significant proteins in the pair-wise comparison between SLD vs. Ctrl was performed. As shown in FIG. 18A, the SLD group was separated entirely from the control group. Next, the proteins driving the separation (the "loadings" of the multidimensional PCA) were examined to identify the proteins with the highest power to separate these two groups. These proteins with the highest discriminating power are highlighted in FIG. 18B and tabulated in Table 4. The proteins on the far right of FIG. 18B include acute-phase proteins (such as SAA1/2/3, Orm2, and Hp) and bacterial lipopolysaccharide-binding proteins [such as proteoglycan 4 and monocyte differentiation antigen CD14]. The proteins that have the highest discriminating power between LD vs. Ctrl groups were also identified by PCA analysis (FIGS. 19C and 19D, Table 4). Many proteins that differentiated LD from controls overlap with the proteins that separated SLD group from the control group. PCA analysis identified 17 proteins that can differentiate the LD group from SLD group, including uteroglobin (Scgb1a1), creatine kinase M-type (Ckm), and plasminogen activator inhibitor 1 (Serpine1) (FIGS. 18E and 18F, Table 4).

Figure 13:
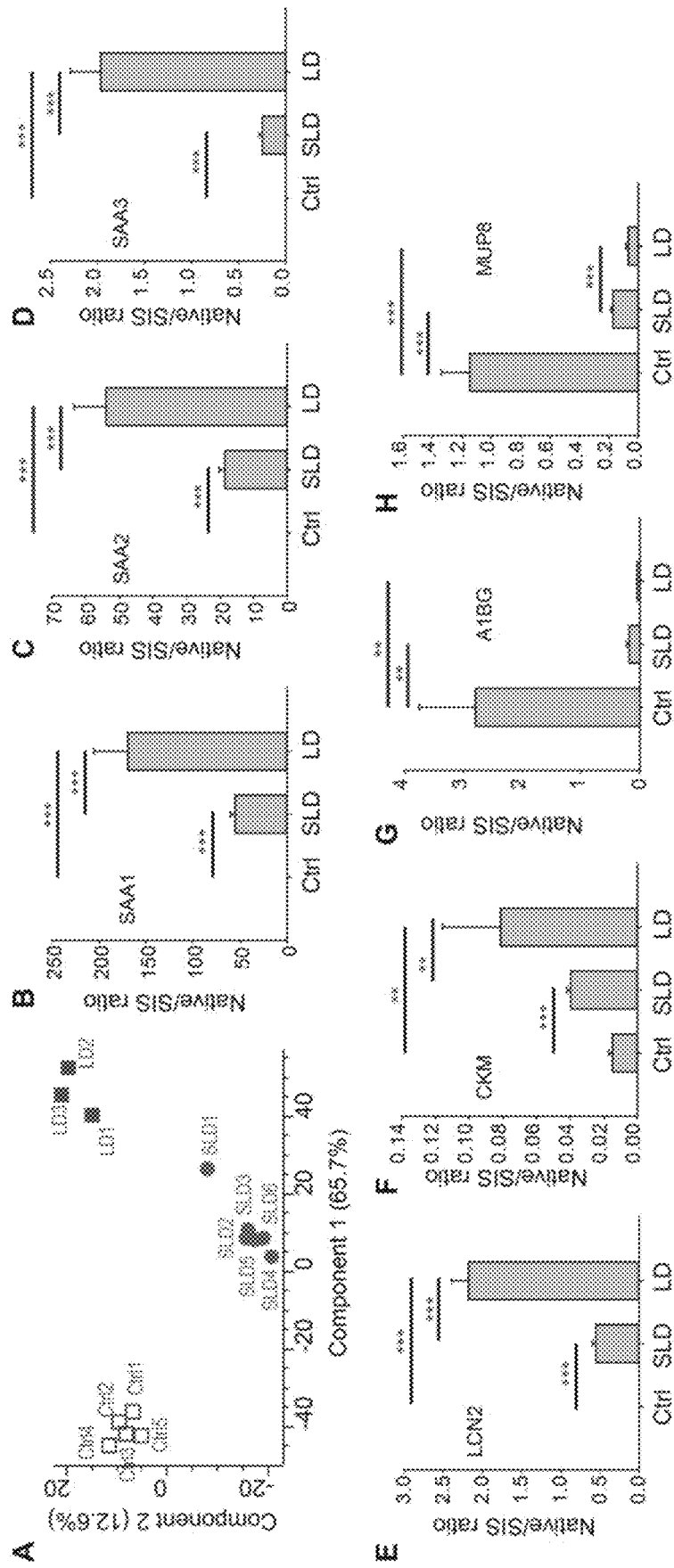
FIG. 13. Identification of plasma protein markers for R. conorii infection. (A) PCA analysis of plasma proteins that were significantly changed by sub-lethal dose (SLD, n=6) and lethal-dose (LD, n=3) of R. conorii infection. Blue open squares are control animals (Ctrl, n=5), red solid circles are individual animals with SLD R. conorii infection, and green solid squares are animals with lethal dose R. conorii infection. (B)-(H) SID-SRM-MS validation of plasma protein markers for R. conorii infection and the severity of the infection. , p-value<0.05; *, p-value<0.001.

Several protein markers were selected including Saa1/2/3, Lcn2, Ckm, Albg, and Mup8 for further validation with quantitative SID-SRM-MS assays. As shown in FIG. 13B-13H, SID-SRM-MS analysis confirmed the result from the label-free proteomics analysis. For example, the abundance of Saa1/2/3, Lcn2, and Ckm were significantly elevated by R. conorii infection (FIGS. 13B-13F), and the magnitude of up-regulation increased with the severity of infection. Meanwhile, SID-SRM-MS confirmed the down-regulation of Albg and Mup8 by R. conorii infection (FIGS. 13G, 13H).

Figure 14:
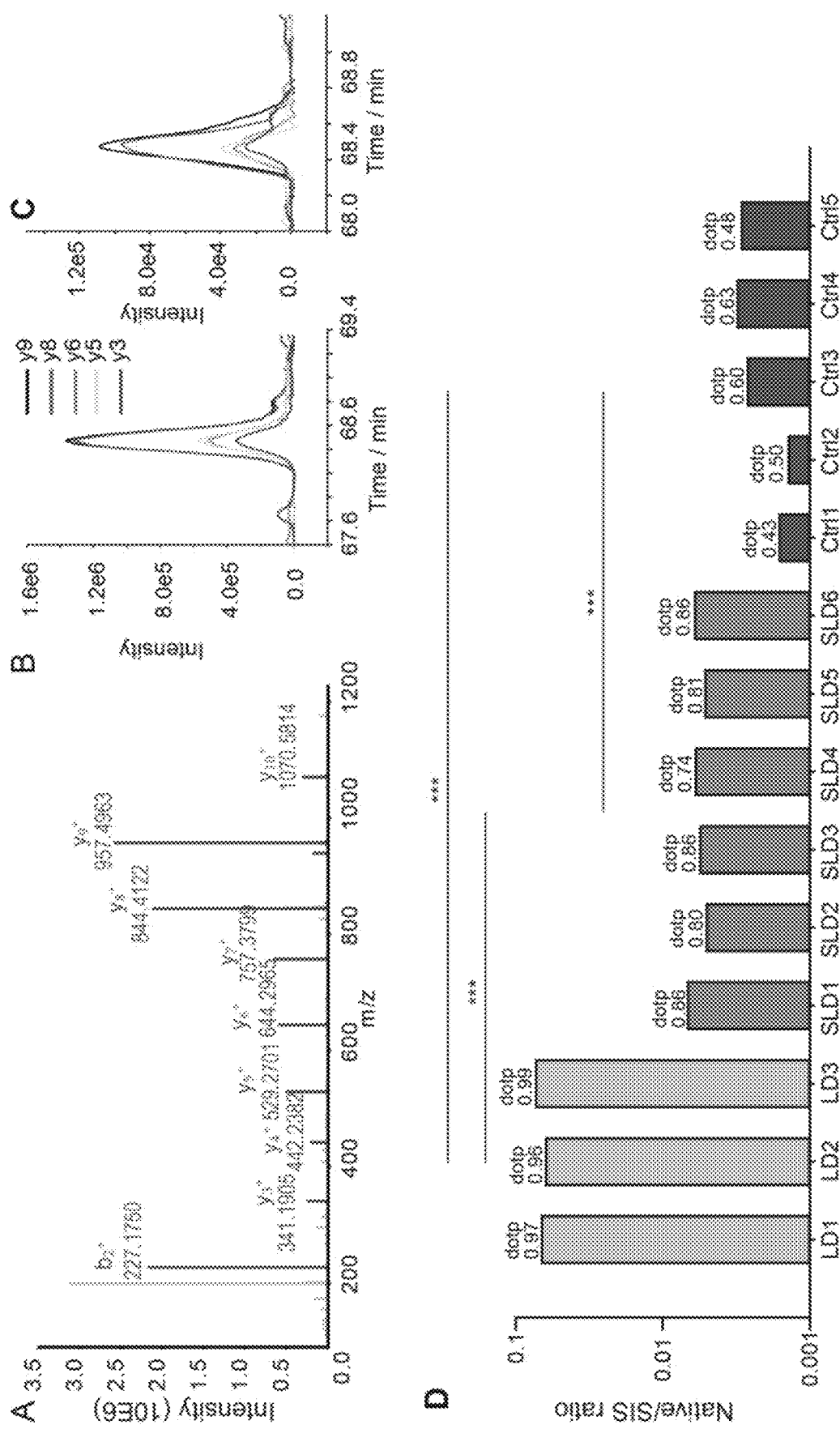
FIG. 14. SID-PRM-MS validation of rickettsial protein RC0497. (A) Annotated MS/MS spectrum of stable isotope labeled RC0497 peptide LLLSLDSTGE[K(13C6,15N2)]. (B) LC chromatogram for transitions of stable isotope-labeled standard peptide LLLSLDSTGE[K(13C6,15N2)]. (C) LC chromatogram for transitions of native peptide LLLSLDSTGEK from the serum of mice with lethal dose rickettsial infection. (D) SID-PRM-MS quantification of RC0497 peptide LLLSLDSTGEK in the mouse serum. The y-axis uses a log 10 scale. Dot-product (dotp) values show the expected similarity in peak shape of native peptides to the library spectra. LD, lethal dose; SLD, sub-lethal dose; Ctrl, control mice. *, p-value<0.001; , p-value<0.05.

SID-parallel reaction monitoring (PRM)-MS analysis of rickettsia RC0497 protein in mouse plasma. In the analysis of the plasma proteome of the animals infected with R. conorii, no rickettsial protein was identified, including RC0497, probably due to their low-abundance in the mouse plasma. To increase the sensitivity of detection, a targeted SID-PRM assay was developed for RC0497. The stable isotope labeled RC0497 signature peptide LLLSLDSTGE[K($^{13}C_6$,$^{15}N_2$)] of RC0497 was used to determine the best PRM transitions for this peptide (FIG. 14A). Extracted ion chromatograms (EIC) for transitions of LLLSLDSTGE[K($^{13}C_6$,$^{15}N_2$)] and their unlabeled counterparts yielded by tryptic digest from the plasma from mice infected with LD of R. conorii are shown in FIGS. 14B and 14C. The similarity in peak shape and retention time of native RC0497 peptide and the stable isotope labeled standard peptides was examined. The EIC of the native RC0497 peptide from the plasma of the animal with lethal R. conorii infection (FIG. 14C) are remarkably similar to that of the standard peptide (FIG. 14B). The dot product (dotp) value was used to quantitatively measure the degree of the match between spectral library MS/MS and the EIC of the corresponding transitions of peptide LLLSLDSTGEK (SEQ ID NO:3). A high dotp value (ranging from a value of 0-1) indicates a better match and the absence of interfering signals. As shown in FIG. 14D, the PRM measurement of RC0497 peptides from lethal-dose samples has superior dotp values (>0.95), indicating the unambiguous identification of RC0497 peptide; five out six SLD samples have dotp values higher than 0.8; dotp values of uninfected samples were 0.3-0.63 which indicates the absence of the peptides in the sample. Together, the PRM data was interpreted to confirm the presence of RC0497 in the plasma of R. conorii-infected animals. Moreover, RC0497 abundance is positively correlated with the load of R. conorii and severity of the infection. Because the RC0497 is unique to Rickettsia, and the most highly abundant rickettsial protein in the endothelial secretome, it is an ideal biomarker candidate for the diagnosis of acute rickettsial infections.

Figure 19:
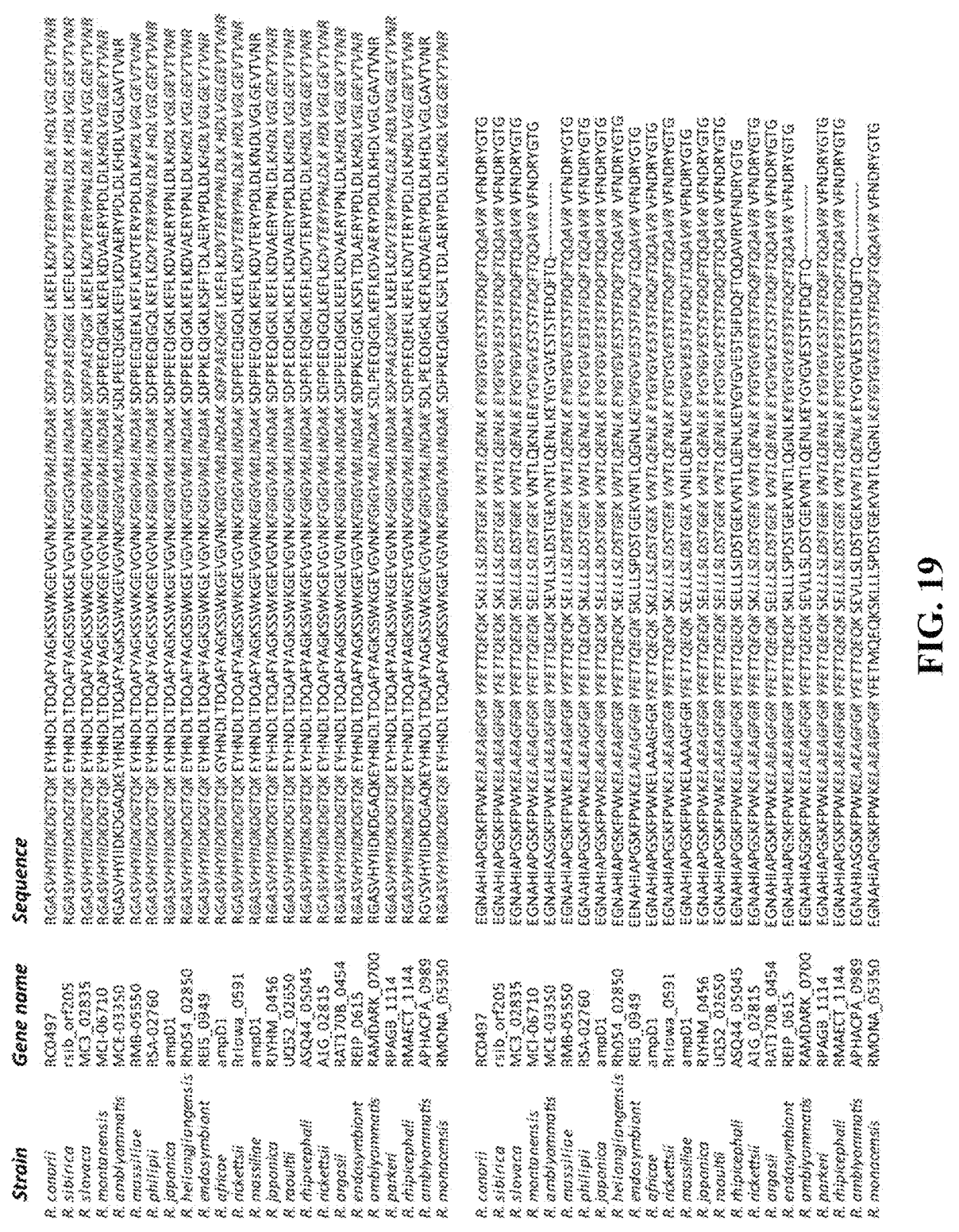

Conservation of RC0497 in major spotted fever group rickettsiae. In this study, RC0497 was identified in the conditioned medium of HUVECs infected with R. conorii. To determine whether this protein was conserved in other rickettsial strains, a protein sequence alignment analysis was conducted. It was found that protein RC0497 is highly conserved across diverse rickettsial strains including R. rickettsii, the causative agent of the Rocky Mountain spotted fever (RMSF) (FIG. 19). RC0497 was identified with ten peptides in the study of the secretome of HUVECs. In addition to R. conorii and R. rickettsii, the diagnostic peptides are found in R. conorii, R. rickettsii, R. monacensis, R. amblyommates, R. parkeri, R. sibirica, R. africae, R. phihpii, R. japonica and others (FIG. 19). These data were interpreted to indicate that detection of RC0497 can be used for diagnosis of a wide variety of rickettsial spotted fever infection and that our targeted SRM- or PRM-MS assays could be directly transferrable.

Figure 20:
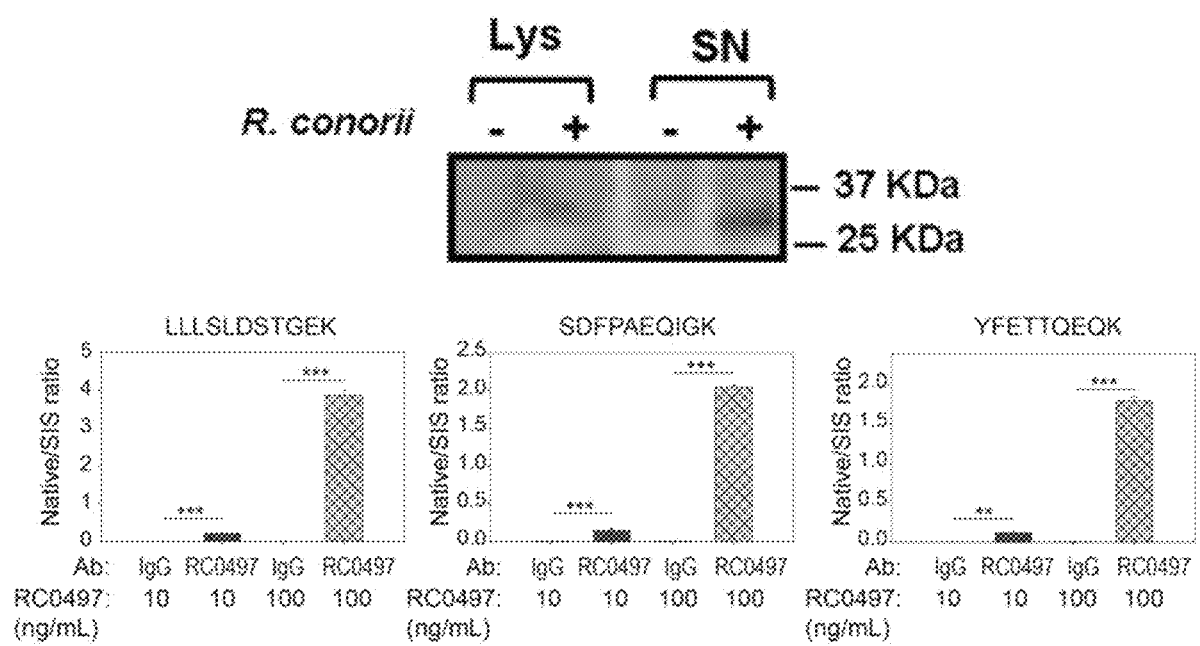
FIG. 20. The evaluation of the antibody against Rickettsia RC0497 protein. (A) Detection of RC0497 in the supernatant of Rickettsia Conorii-infected HUVECs by a rabbit polyclonal antibody directed against recombinant RC0497. Lys, cell lysate; SN, supernatant of conditioned medium. (B) IP-SRM analysis of RC0497 using anti-RC0497 antibody. IgG was used as the negative control. The RC0497 was pulldown by anti-RC0497 antibody or IgG, respectively, and then three RC0497 peptides were measured with SID-SRM-MS.

Verification of RC0497 and host proteins in the serum from patients with acute rickettsiosis. Verification of the presence of RC0497 was attempted in the serum of patients with rickettsial infection with targeted MS analysis, but it was found that the level of RC0497 in the serum of patients with rickettsial infection is much lower than the in vivo model, and the sensitivity of PRM or SRM were not enough for detecting RC0497 in patients' serum. To increase the sensitivity of the assay, an immunoprecipitation (IP)-SRM assay was developed in which the RC0497 protein was captured from serum with an RC0497 specific antibody and followed by SRM analysis of the enriched protein. Because there is no commercial RC0497 antibody, a polyclonal antibody was developed that is directed against RC0497. The reactivity and specificity of the antibody against RC0497 were first examined using immunoblotting. The culture medium and cell lysate of HUVECs infected with R. conorii were collected. The presence of RC0497 in the medium and cell lysate was probed with the anti-RC0497 antibody. The culture medium and cell lysate collected from uninfected cells were used as control. As shown in FIG. 20A, RC0497 was detected from the culture medium and cell lysate of HUVECs infected with R. conorii and no significant signal was detected in the negative controls, suggesting that the anti-RC0497 antibody has excellent reactivity and specificity against RC0497. Next, feasibility tests were conducted to determine whether this antibody was useful for immunoprecipitation. Recombinant RC0497 was spiked into human serum at the concentrations of 10 ng/mL and 100 ng/mL. Then RC0497 protein was exposed to the anti-RC0497 antibody or control IgG, respectively, and pulldown with proteinA/G beads. The proteins captured on the beads were digested with trypsin. The abundance of RC0497 pulldown was measured by anti-RC0497 antibody or IgG with SID-SRM-MS. As shown in FIG. 20B, the RC0497 was significantly enriched by anti-RC0497 antibody relative to negative control IgG. These data suggest that anti-RC0497 antibody efficiently pulldown RC0497 and can be used for IP-SRM-MS analysis.

Figure 15:
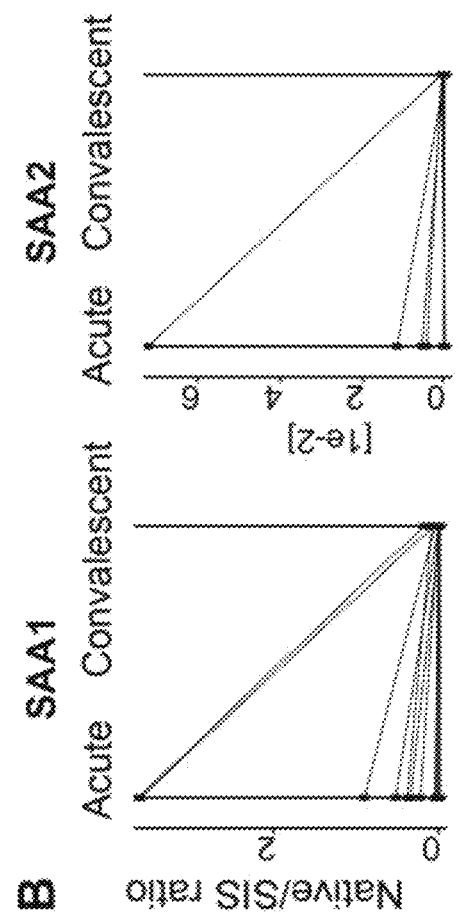
FIG. 15. Quantification of RC0497 and host proteins in serum from patients infected with Rickettsia conorii. (A) SID-SRM-MS analysis of RC0497. (B) SID-SRM-MS analysis of serum amyloid A-1 protein (SAA1) and serum amyloid A-2 protein (SAA2).
Figure 15:
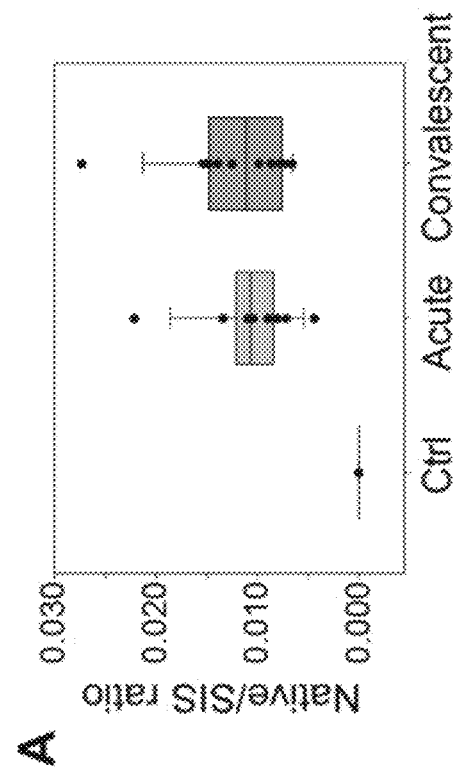

Next, 13 de-identified paired serum samples (acute and convalescent) from confirmed cases of Mediterranean spotted fever collected from discarded diagnostic material were used. Serum samples from six healthy individuals free of rickettsial infection were used as control. The diagnosis of MSF infection was made with IFA. IP-SRM-MS assay described above was used to measure the abundance of RC0497 in these samples. As shown in FIG. 15A, the level of RC0497 was elevated in the serum samples from patients with acute MSF relative to healthy controls. The level of RC0497 in the serum samples from convalescent patients was also elevated relative to healthy controls, and in some cases, the level of RC0497 was even higher than that in the paired acute samples.

Also, SRM assays were developed for human host proteins SAA1 and SAA2. Both proteins were significantly up-regulated in the serum of mice infected with R. conorii. The level of these two proteins was measured in the paired human serum collected during the acute phase and convalescence of R. conorii infection. As shown in FIG. 15B, compared to convalescence, the level of SAA1 and SAA2 were markedly elevated, suggesting that the acute response reactants were activated during the early stage of infection and were cleared during convalescence.

The invention claimed is:

1. A method for detecting acute phase Rickettsial protein RC0497 in a sample comprising:

contacting the sample with antibodies that bind Rickettsial protein RC0497 (SEQ ID NO:1) or Rickettsial protein RC0497 peptides forming an antibody complex with RC0497 peptides in the sample or RC0497 reactive antibodies in the sample, respectively;

isolating the antibody complex; and identifying the peptides present in the antibody complex.

2. The method of claim 1, wherein the peptides are HDLVGLGEVTVNR (SEQ ID NO:2), LLLSLDSTGEK (SEQ ID NO:3), ELAEAGFGR (SEQ ID NO:4), SDFPAEQIGK, (SEQ ID NO:5), EYHNDLTDQAFYAGK (SEQ ID NO:6), EYGYGVESTSTFDQFTQQAVR (SEQ ID NO:7), and/or GASVHYIIDK (SEQ ID NO:8).

3. The method of claim 1, wherein the peptides are identified by selected reaction monitoring (SRM).

4. The method of claim 1, wherein the antibody is a polyclonal antibody.

5. The method of claim 1, wherein the Rickettsial protein RC0497 is a *R. africae, R. conorii, or R. parkeri* Rickettsial protein RC0497.

6. The method of claim 1, further comprising detecting at least one host response protein selected from BPI fold-containing family A member 2, Histone H3.3, Ferritin heavy chain, 4-hydroxy-phenylpyruvate dioxygenase, or Adenylyl cyclase-associated protein 1.

* * * * *

SEQUENCE LISTING

<160> NUMBER OF SEQ ID NOS: 10

<210> SEQ ID NO 1
<211> LENGTH: 267
<212> TYPE: PRT
<213> ORGANISM: Rickettsia rickettsii

<400> SEQUENCE: 1

Met Ser Lys Ser Lys Ala Ile Glu Asn Asn Gly Ile Ser Asn Thr Asn
1               5                   10                  15

Ser Pro Asn Gly Lys Tyr Met Ala Pro Arg Pro Glu Gly Val Lys Pro
            20                  25                  30

Thr Cys Val Val Ile Thr Tyr Ser Val Ser Lys Asp Ile Lys Ala Val
        35                  40                  45

Arg Glu Val Leu Asp Glu Arg Gly Ala Ser Val His Tyr Ile Ile Asp
    50                  55                  60

Lys Asp Gly Thr Gln Lys Glu Tyr His Asn Asp Leu Thr Asp Gln Ala
65                  70                  75                  80

Phe Tyr Ala Gly Lys Ser Ser Trp Lys Gly Glu Val Gly Val Asn Lys
                85                  90                  95

Phe Gly Ile Gly Val Met Leu Ile Asn Asp Ala Lys Ser Asp Phe Pro
            100                 105                 110

Ala Glu Gln Ile Gly Lys Leu Lys Glu Phe Leu Lys Asp Val Thr Glu
        115                 120                 125

Arg Tyr Pro Asn Leu Asp Leu Lys His Asp Leu Val Gly Leu Gly Glu
    130                 135                 140

Val Thr Val Asn Arg Glu Gly Asn Ala His Ile Ala Pro Gly Ser Lys
145                 150                 155                 160

Phe Pro Trp Lys Glu Leu Ala Glu Ala Gly Phe Gly Arg Tyr Phe Glu
                165                 170                 175

Thr Thr Gln Glu Gln Lys Ser Lys Leu Leu Ser Leu Asp Ser Thr
            180                 185                 190

Gly Glu Lys Val Asn Thr Leu Gln Glu Asn Leu Lys Glu Tyr Gly Tyr
    195                 200                 205

Gly Val Glu Ser Thr Ser Thr Phe Asp Gln Phe Thr Gln Gln Ala Val
    210                 215                 220

Arg Val Phe Asn Asp Arg Tyr Gly Thr Gly Leu Pro Asn Glu Glu Pro
225                 230                 235                 240

Pro Val Ser Trp Thr Glu Ala Gly Gln Asp Val Leu Ser Gln Leu Leu
                245                 250                 255

Gly Gln Thr Val Leu Glu Gln Thr Glu Asn Ala
            260                 265

<210> SEQ ID NO 2
<211> LENGTH: 13
<212> TYPE: PRT
<213> ORGANISM: Artificial Sequence
<220> FEATURE:
<223> OTHER INFORMATION: synthetic peptide

<400> SEQUENCE: 2

His Asp Leu Val Gly Leu Gly Glu Val Thr Val Asn Arg
1               5                   10

<210> SEQ ID NO 3
<211> LENGTH: 11
<212> TYPE: PRT
<213> ORGANISM: Artificial Sequence

```
<220> FEATURE:
<223> OTHER INFORMATION: synthetic peptide

<400> SEQUENCE: 3

Leu Leu Leu Ser Leu Asp Ser Thr Gly Glu Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Glu Leu Ala Glu Ala Gly Phe Gly Arg
1               5

<210> SEQ ID NO 5
<211> LENGTH: 10
<212> TYPE: PRT
<213> ORGANISM: Artificial Sequence
<220> FEATURE:
<223> OTHER INFORMATION: synthetic peptide

<400> SEQUENCE: 5

Ser Asp Phe Pro Ala Glu Gln Ile Gly Lys
1               5                   10

<210> SEQ ID NO 6
<211> LENGTH: 15
<212> TYPE: PRT
<213> ORGANISM: Artificial Sequence
<220> FEATURE:
<223> OTHER INFORMATION: synthetic peptide

<400> SEQUENCE: 6

Glu Tyr His Asn Asp Leu Thr Asp Gln Ala Phe Tyr Ala Gly Lys
1               5                   10                  15

<210> SEQ ID NO 7
<211> LENGTH: 21
<212> TYPE: PRT
<213> ORGANISM: Artificial Sequence
<220> FEATURE:
<223> OTHER INFORMATION: synthetic peptide

<400> SEQUENCE: 7

Glu Tyr Gly Tyr Gly Val Glu Ser Thr Ser Thr Phe Asp Gln Phe Thr
1               5                   10                  15

Gln Gln Ala Val Arg
            20

<210> SEQ ID NO 8
<211> LENGTH: 10
<212> TYPE: PRT
<213> ORGANISM: Artificial Sequence
<220> FEATURE:
<223> OTHER INFORMATION: synthetic peptide

<400> SEQUENCE: 8

Gly Ala Ser Val His Tyr Ile Ile Asp Lys
1               5                   10

<210> SEQ ID NO 9
<211> LENGTH: 267
```

```
<212> TYPE: PRT
<213> ORGANISM: Rickettsia conorii

<400> SEQUENCE: 9

Met Ser Lys Ser Lys Ala Ile Glu Asn Asn Gly Ile Ser Asn Thr Asn
1               5                   10                  15

Ser Pro Asn Gly Lys Tyr Met Ala Pro Arg Pro Glu Gly Val Lys Pro
            20                  25                  30

Thr Cys Val Val Ile Thr Tyr Ser Val Ser Lys Asp Ile Lys Ala Val
        35                  40                  45

Arg Glu Val Leu Asp Glu Arg Gly Ala Ser Val His Tyr Ile Ile Asp
    50                  55                  60

Lys Asp Gly Thr Gln Lys Glu Tyr His Asn Asp Leu Thr Asp Gln Ala
65                  70                  75                  80

Phe Tyr Ala Gly Lys Ser Ser Trp Lys Gly Glu Val Gly Val Asn Lys
                85                  90                  95

Phe Gly Ile Gly Val Met Leu Ile Asn Asp Ala Lys Ser Asp Phe Pro
            100                 105                 110

Ala Glu Gln Ile Gly Lys Leu Lys Glu Phe Leu Lys Asp Val Thr Glu
        115                 120                 125

Arg Tyr Pro Asn Leu Asp Leu Lys His Asp Leu Val Gly Leu Gly Glu
    130                 135                 140

Val Thr Val Asn Arg Glu Gly Asn Ala His Ile Ala Pro Gly Ser Lys
145                 150                 155                 160

Phe Pro Trp Lys Glu Leu Ala Glu Ala Gly Phe Gly Arg Tyr Phe Glu
                165                 170                 175

Thr Thr Gln Glu Gln Lys Ser Lys Leu Leu Leu Ser Leu Asp Ser Thr
            180                 185                 190

Gly Glu Lys Val Asn Thr Leu Gln Glu Asn Leu Lys Glu Tyr Gly Tyr
        195                 200                 205

Gly Val Glu Ser Thr Ser Thr Phe Asp Gln Phe Thr Gln Gln Ala Val
    210                 215                 220

Arg Val Phe Asn Asp Arg Tyr Gly Thr Gly Leu Pro Asn Glu Glu Pro
225                 230                 235                 240

Pro Val Ser Trp Thr Glu Ala Gly Gln Asp Val Leu Ser Gln Leu Leu
                245                 250                 255

Gly Gln Thr Val Leu Glu Gln Thr Glu Asn Ala
            260                 265

<210> SEQ ID NO 10
<211> LENGTH: 267
<212> TYPE: PRT
<213> ORGANISM: Rickettsia rickettsia

<400> SEQUENCE: 10

Met Ser Lys Ser Lys Ala Ile Glu Asn Asn Gly Ile Ser Asn Thr Asn
1               5                   10                  15

Ser Pro Asn Cys Lys Tyr Met Ala Pro Arg Pro Glu Gly Val Lys Pro
            20                  25                  30

Thr Cys Val Val Ile Thr Tyr Ser Val Ser Lys Asp Ile Lys Thr Val
        35                  40                  45

Arg Glu Val Leu Asp Glu Arg Gly Ala Ser Val His Tyr Ile Ile Asp
    50                  55                  60

Lys Asp Gly Thr Gln Lys Glu Tyr His Asn Asp Leu Thr Asp Gln Ala
65                  70                  75                  80
```

-continued

```
Phe Tyr Ala Gly Lys Ser Ser Trp Lys Gly Glu Val Gly Val Asn Lys
                85                  90                  95

Phe Gly Ile Gly Val Met Leu Ile Asn Asp Ala Lys Ser Asp Phe Pro
            100                 105                 110

Glu Glu Gln Ile Gly Gln Leu Lys Glu Phe Leu Lys Asp Val Thr Glu
        115                 120                 125

Arg Tyr Pro Asn Leu Asp Leu Lys His Asp Leu Val Gly Leu Gly Glu
    130                 135                 140

Val Thr Val Asn Arg Glu Gly Asn Ala His Ile Ala Pro Gly Ser Lys
145                 150                 155                 160

Phe Pro Trp Lys Glu Leu Ala Glu Ala Gly Phe Gly Arg Tyr Phe Glu
                165                 170                 175

Thr Thr Gln Glu Gln Lys Ser Lys Leu Leu Leu Ser Leu Asp Ser Thr
            180                 185                 190

Gly Glu Lys Val Asn Thr Leu Gln Glu Asn Leu Lys Glu Tyr Gly Tyr
        195                 200                 205

Gly Val Glu Ser Thr Ser Thr Phe Asp Gln Phe Thr Gln Gln Ala Val
    210                 215                 220

Arg Val Phe Asn Asp Arg Tyr Gly Thr Gly Leu Pro Asn Glu Glu Pro
225                 230                 235                 240

Pro Val Ser Trp Thr Glu Ala Gly Gln Asp Val Leu Ser Gln Leu Leu
                245                 250                 255

Gly Gln Thr Val Leu Glu Gln Thr Glu Asn Ala
            260                 265
```